United States Patent [19]

Torelli et al.

[11] Patent Number: 4,701,449
[45] Date of Patent: Oct. 20, 1987

[54] NOVEL 10-SUBSTITUTED STEROIDS AND THEIR USE IN THE INDUCTION OF ALDOSTERONE ANTAGONISTIC ACTIVITY

[75] Inventors: Vesperto Torelli, Maisons Alfort; Lucien Nedelec, Le Raincy; Martine Moguilewski, Nogent Sur Marne; Anne-Marie Moura, Paris, all of France

[73] Assignee: Roussel Uclaf, Paris, France

[21] Appl. No.: 768,867

[22] Filed: Aug. 23, 1985

[30] Foreign Application Priority Data

Aug. 24, 1984 [FR] France ............................... 84 13189

[51] Int. Cl.$^4$ .................. A61K 31/585; A61K 31/56; C07J 1/00
[52] U.S. Cl. ..................................... 514/175; 514/179; 260/397.3; 260/397.45; 540/44; 540/45
[58] Field of Search .............. 260/239.55 R, 239.57, 260/397.3, 397.45; 514/175, 179; 540/44, 45

[56] References Cited

U.S. PATENT DOCUMENTS 3,102,127  8/1963  Bowers ............................ 260/397.4
3,218,316  11/1965  Edwards .......................... 260/397.4
3,275,622  9/1966  Bowers ............................ 260/397.4

FOREIGN PATENT DOCUMENTS 1519387  3/1968  France .
2078749  1/1982  United Kingdom .

OTHER PUBLICATIONS

Journal of the American Chemical Society, vol. 79 (1957) No. 17, pp. 4808–4809; Cella et al.
Steroils, vol. 39 (1982) No. 3, pp. 325–344; Marcotte et al.
Chemical Abstracts; vol. 95, #133237r; Teutsch et al.
Chemical Abstracts; vol. 95, #98147n; Nedelec et al.

Primary Examiner—Leonard Schenkman
Assistant Examiner—Joseph A. Lipovsky
Attorney, Agent, or Firm—Bierman & Muserlian

[57] ABSTRACT

Novel 10-substituted steroids of the formula

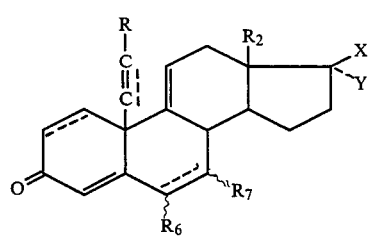

wherein R is selected from the group consisting of hydrogen, alkyl and substituted alkyl of 1 to 8 carbon atoms, alkenyl, substituted alkenyl, alkynyl and substituted alkynyl of 2 to 8 carbon atoms, aryl and substituted aryl, aralkyl and substituted aralkyl, protected hydroxy, optionally esterified carboxy, —NH$_2$, protected amino, mono and di-alkyl amino of 1 to 4 alkyl carbon atoms, halogen and trialkylsilyl, R$_2$ is methyl or ethyl, R$_6$ and R$_7$ together with the carbon atoms to which they are attached form cyclopropyl or R$_6$ is hydrogen and R$_7$ is R$_1$, R$_1$ is selected from the group consisting of hydrogen, alkyl and substituted alkyl of 1 to 6 carbon atoms, acetylthio and alkenyl, substituted alkenyl, alkynyl and substituted alkynyl of 2 to 6 carbon atoms, X is optionally acylated or etherified hydroxyl and Y is selected from the group consisting of hydrogen, R$_4$, —CH$_2$—CH$_2$COOM and —CH$_2$—CH$_2$—CH$_2$OH, M is hydrogen, alkali metal or —NH$_4$ or X and Y together form a member of the group consisting of

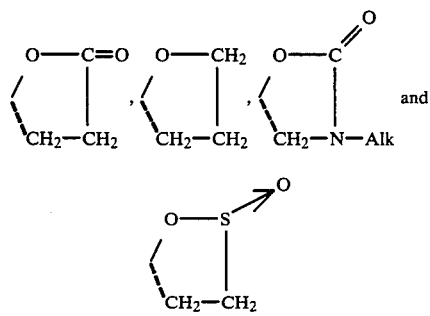

or X is —OH and Y is

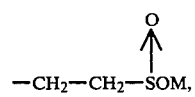

R$_4$ is selected from the group consisting of alkyl of 1 to 6 carbon atoms and alkenyl and alkynyl of 2 to 6 carbon atoms, Alk is alkyl of 1 to 8 carbon atoms, the dotted lines in the 1(2) and 6(7) indicate the optional presence of a second carbon-carbon bond with the proviso that when R$_6$ and R$_7$ form cyclopropyl, there is no 6(7) second bond, the dotted line in 10-substituent indicates the optional presence of a third carbon-carbon bond, the wavy lines at R$_6$ and R$_7$ indicate the possible α- or β-position with the proviso that R is not hydrogen when R$_6$ and R$_7$ are hydrogen R$_2$ is methyl, X is hydroxy or acetoxy and Y is hydrogen, the dotted lines at 1(2) and 6(7) do not represent a second bond and the dotted line in the 10-substituent is a third carbon-carbon bond useful as aldosterone antagonists and for increasing hydrosodium diuresis while preserving organic potassium with reduced hormonal side effects.

21 Claims, No Drawings

NOVEL 10-SUBSTITUTED STEROIDS AND THEIR USE IN THE INDUCTION OF ALDOSTERONE ANTAGONISTIC ACTIVITY

STATE OF THE ART

Related steroids are described in U.S. Pat. Nos. 3,218,316; 3,275,622 and 3,102,127; French Pat. No. 1,519,387; English Pat. No. 2,078,749 and J.A.C.S., Vol. 79 (1957), No. 17, p. 4808–9 and steroid, Vol. 39 (1982) No. 3, p. 325–344.

OBJECTS OF THE INVENTION

It is an object of the invention to provide the novel steroids of formula I and a process for the preparation thereof and novel intermediates.

It is another object of the invention to provide novel compositions for and a novel method of treating arterial hypertension and cardiac deficencies.

These and other objects and advantages of the invention will become obvious from the following detailed description.

THE INVENTION

The novel compounds of the invention are 10-substituted steroids of the formula

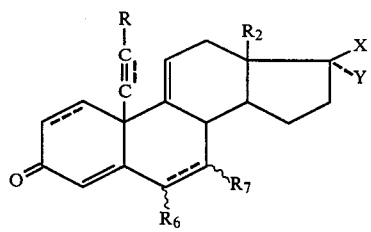

wherein R is selected from the group consisting of hydrogen, alkyl and substituted alkyl of 1 to 8 carbon atoms, alkenyl, substituted alkenyl, alkynyl and substituted alkynyl of 2 to 8 carbon atoms, aryl and substituted aryl, aralkyl and substituted aralkyl, protected hydroxy, optionally esterified carboxy, $-NH_2$, protected amino, mono and di-alkyl amino of 1 to 4 alkyl carbon atoms, halogen and trialkylsilyl, $R_2$ is methyl or ethyl, $R_6$ and $R_7$ together with the carbon atoms to which they are attached form cyclopropyl or $R_6$ in hydrogen and $R_7$ is $R_1$, $R_1$ is selected from the group consisting of hydrogen, alkyl and substituted alkyl of 1 to 6 carbon atoms, acetylthio and alkenyl, substituted alkenyl, alkynyl and substituted alkynyl of 2 to 6 carbon atoms, X is optionally acylated or etherified hydroxyl and Y is selected from the group consisting of hydrogen, $R_4$, $-CH_2-CH_2COOM$ and $-CH_2-CH_2-CH_2OH$, M is hydrogen, alkali metal or $-NH_4$ or X and Y together form a member of the group consisting of

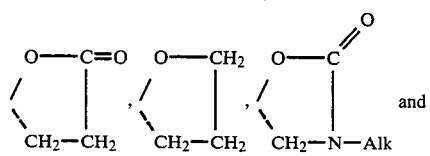

and

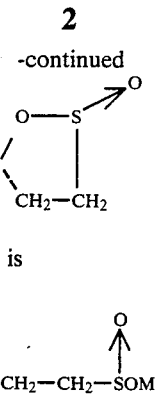

or X is $-OH$ and Y is $-CH_2-CH_2-SOM$, $R_4$ is selected from the group consisting of alkyl of 1 to 6 carbon atoms and alkenyl and alkynyl of 2 to 6 carbon atoms, Alk is alkyl of 1 to 8 carbon atoms, the dotted lines in the 1(2) and 6(7) indicate the optional presence of a second carbon-carbon bond with the proviso that when $R_6$ and $R_7$ form cyclopropyl, there is no 6(7) second bond, the dotted line in 10-substitutent indicates the optional presence of a third carbon-carbon bond, the wavy lines at $R_6$ and $R_7$ indicate the possible α- or β-position with the proviso that R is not hydrogen when $R_6$ and $R_7$ are hydrogen $R_2$ is methyl, X is hydroxy or acetoxy and Y is hydrogen, the dotted lines at 1(2) and 6(7) do not represent a second bond and the dotted line in the 10-substituent is a third carbon-carbon bond.

Among the preferred compounds of formula I are those of the formula

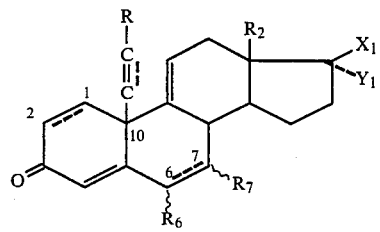

wherein R, $R_2$, $R_6$ and $R_7$ have the above definition, $X_1$ is $-OH$ and $Y_1$ is $-CH_2-CH_2-COOM$ or $-CH_2-CH_2-CH_2OH$, M has the above definition or $X_1$ and $Y_1$ together form

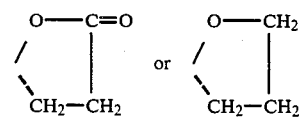

or $X_1$ is optionally acrylated or etherified hydroxyl and $Y_1$ is hydrogen or $R_4$ and $R_4$ has the above definition and the dotted lines in the 1(2) and 6(7) and in the 10-substituent have the above definition and the wavy lines have the above definition with the proviso that R is not hydrogen when $R_6$ and $R_7$ are hydrogen, $R_2$ is methyl, $X_1$ is $-OH$ or acetoxy, $Y_1$ is hydrogen and the 1(2) and 6(7) positions are saturated and the dotted line in the 10-substituent is a third carbon-carbon bond.

Examples of R are alkyl such as methyl, ethyl, n-propyl, isopropyl, butyl, sec.-butyl, tert.-butyl, and branched and linear pentyl, hexyl, heptyl and octyl; alkenyl such as vinyl, allyl, 1-propenyl and butenyl; and alkynyl such as ethynyl, propargyl and butynyl; all of which may be substituted with at least one member of the group consisting of —OH, possibly esterified carboxy such as methoxycarbonyl and ethoxycarbonyl, optionally protected amino such as tritylamino, chloroacetylamino, trifluoroacetylamino and trichloroethoxycarbonylamino, monoalkyl or dialkylamino such as methylamino and dimethylamino, halogen, preferably chlorine or bromine.

The aryl and aralkyl of R can also be preferably phenyl, benzyl or phenylethyl which can also be substituted, for example by at least one of the following: hydroxyl, optionally esterified carboxy, amino, mono- or dialkylamino, alkyl such as methyl, alkoxy such as methoxy and alkylthio such as methylthio. The protected hydroxyl of R can be for example a tetrahydropyranyloxy or tert.-butyloxy radical and the preferred trialkysilyl is the trimethylsilyl The values of $R_1$ and $R_4$ may be chosen from the values cited previously for R. M preferably is sodium, potassium or lithium. When X is an acylated or etherified hydroxyl, the preferred groups are acetyloxy, propionyloxy, methoxy or ethoxy.

When $R_1$ is other than hydrogen, $R_1$ is preferably at position $7\alpha$. The cyclopropyl which $R_6$ and $R_7$ can form with the carbons which carry them is also preferably $6\alpha, 7\beta$.

The compounds of formula I in which X and Y together form

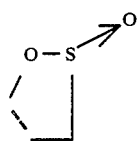

exist in the form of two diastereoisomers at the level of the sulfur, possibly separable from one another and named by convention A and B isomers, isomer A being the isomer whose melting point is the highest.

Among the products of the formula I, the most preferred products are those of the formula

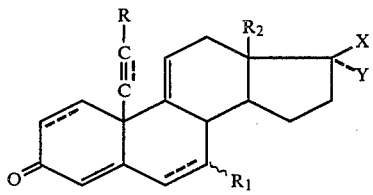

in which R, $R_1$, $R_2$, X and Y, the dotted lines and the wavy lines have the significance indicated above.

Other preferred products of the formula I as described above are those in which R and $R_1$ are chosen from the group consisting of hydroxyl, possibly esterified carboxy, amino, protected amino, mono- or dialkylamino and halogens, those wherein the dotted line in the 10-substituent is a third bond and R is chosen from the group consisting of hydrogen, alkyl of 1 to 3 carbon atoms, methylhydroxyl and phenyl and those wherein $R_1$ is chosen from the group consisting of hydrogen, alkyl of 1 to 4 carbon atoms and acetylthio and X and Y are such that
either X is hydroxy and Y is $CH_2CH_2CO_2M'$ radical in which M' is hydrogen or an alkali metal, or Y is hydrogen, or X and Y form

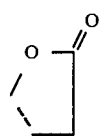

Specific preferred compounds of the invention are
γ-lactone of $10\beta$-ethynyl-19-nor-$17\alpha$-$17\alpha$-$\Delta^{4,9(11)}$-pregnadiene-$17\beta$ol-3-one-21-carboxylic acid,
γ-lactone of $10\beta$-(1-propynyl)-19-nor-$17\alpha$-$\Delta^{4,9(11)}$-pregnadiene-$17\beta$-ol-3-one-21-carboxylic acid,
γ-lactone of $10\beta$-(3-hydroxy-prop-1-ynyl)-19-nor-$17\alpha$-$\Delta^{4,9(11)}$-pregnadiene-$17\beta$-ol-3-one-21-carboxylic acid,
γ-lactone of $10\beta$-ethynyl-$7\alpha$-acetylthio-19-nor-$17\alpha$-$\Delta^{4,9(11)}$-pregnadiene-$17\beta$-ol-3-one-21-carboxylic acid,
γ-lactone of $10\beta$-ethynyl-19-nor-$7\alpha$-propyl-$17\alpha$-$\Delta^{4,9(11)}$-pregnadiene-$17\beta$-ol-3-one-21-carboxylic acid, and
$10\beta$-(prop-1-ynyl)-$\Delta^{4,9(11)}$-estradiene-$17\beta$-ol-3-one.

Among the products, the products most particularly regarded are: γ-lactone of $10\beta$-ethynyl-19-nor-$17\alpha$-$\Delta^{4,9(11)}$-pregnadiene-$17\beta$-ol-3-one-21-carboxylic acid and γ-lactone of $10\beta$-(1-propynyl)-19-nor-$17\alpha$-$\Delta^{4,9(11)}$-pregnadiene-$17\beta$-ol-3-one-21-carboxylic acid.

The novel process of the invention for the preparation of the compounds of formula I comprises reacting a compound of the formula

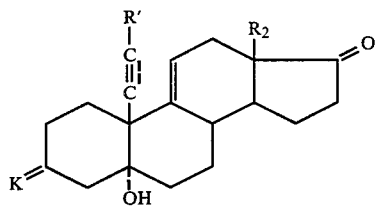

wherein R' is R as defined above or with its reactive groups protected, $R_2$ has the above definition and K is a protected ketone (A) either with a trimethylsulfonium halide in the presence of a strong base, then with a metallic derivative of acetonitrile followed by a base and then an acid or with a compound of the formula

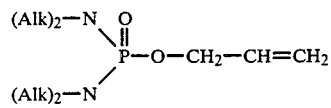

where Alk is alkyl of 1 to 4 carbon atoms in the presence of a strong base and then with an acid to form a compound of the formula

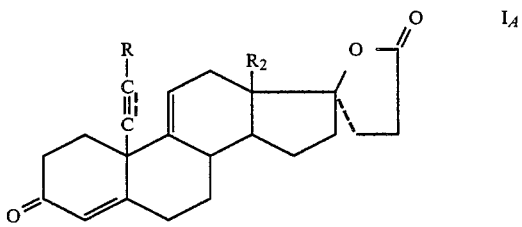

or (B) with a compound of the formula

XMg—CH$_2$—CH$_2$—CH$_2$OB wherein X is halogen and B is a hydroxyl protective group or a magnesium alcoholate followed by acid treatment to form a compound of the formula

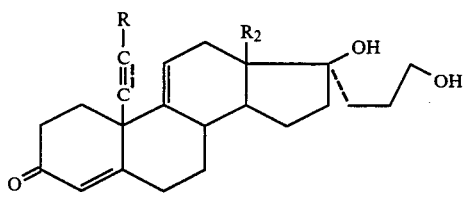  I'$_A$ and optionally heating the latter with a sulfonic acid halide in the presence of a base to form a compound of the formula

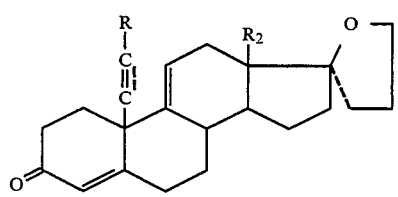  I"$_A$ or (C) with a reducing agent and then with an acid to form a compound of the formula

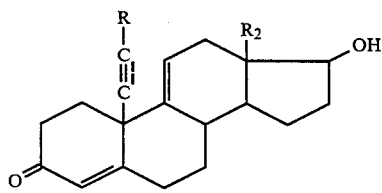  I$_{3A}$ or (D) with an organometallic compound of the formula R$_4$MgX or (R$_4$)$_2$-Cu Li, wherein X is halogen and R$_4$ has the above definitions and then with an acid to form compound of the formula

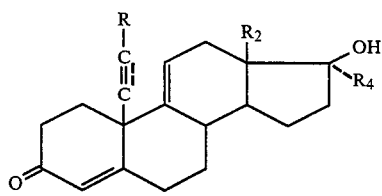  I$_{4A}$ or (E) with a trimethylsulfonium halide in the presence of a strong base, then with an amine of the formula H$_2$N—Alk in the presence of an acid wherein Alk has the above definition and then with an alkyl chloroformate followed by a strong base and then an acid to obtain a compound of the formula

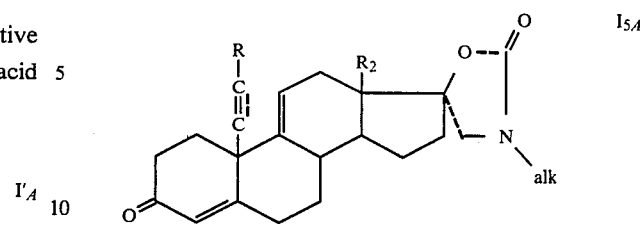  I$_{5A}$ or (F) with a trimethylsulfonium halide in the presence of a strong base and then with tert.-butyl methyl sulfoxide presence of n-butyllithium to form a compound of the formula

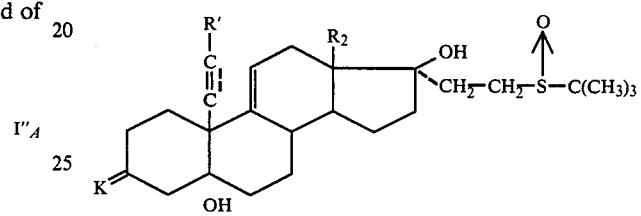

in the form of a mixture of two diastereoisomers about the sulfur atom, optionally separating the two diastereoisomers, then either their mixture, or each separately, is treated with an acid to form a product of the formula

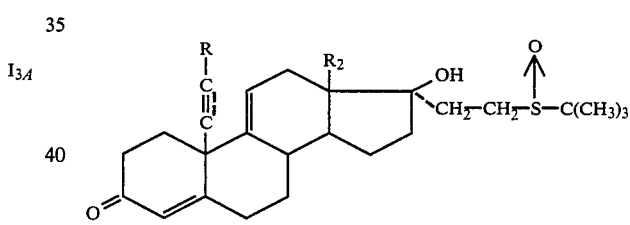

in the form of a mixture of the two diastereoisomers or one diastereoisomer, optionally separating the mixture of the diastereoisomers, then subjecting either the mixture, or the individual isomer to the action of N-chloro or N-bromo-succinimide to obtain a product of the formula

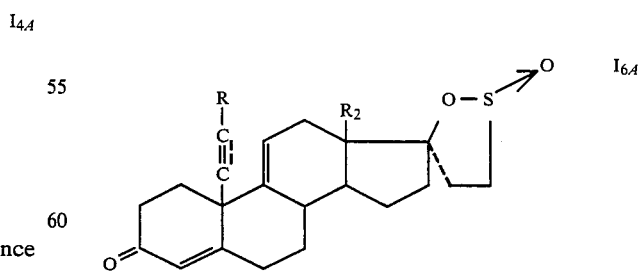  I$_{6A}$ and optionally treating the products of formulae I$_A$, I$_A'$, I$_A''$, I$_{3A}$, I$_{4A}$, I$_{5A}$ and I$_{6A}$ with an alkyl orthoformate in the presence of an acid then with a dehydrogenation agent to obtain the products of the formulae:

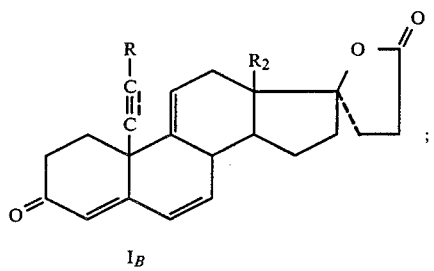

$I_B$

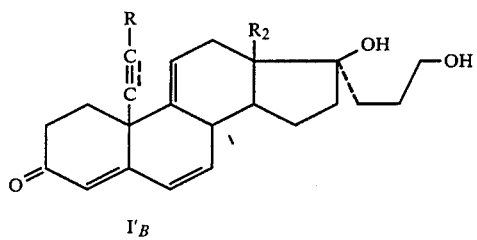

$I'_B$

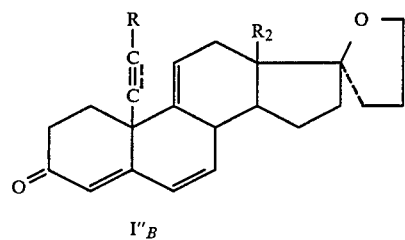

$I''_B$

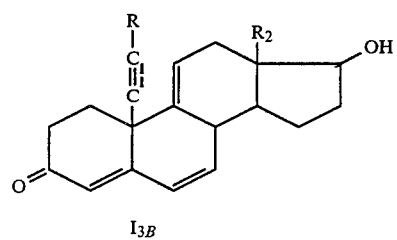

$I_{3B}$

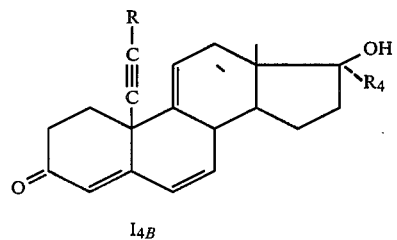

$I_{4B}$

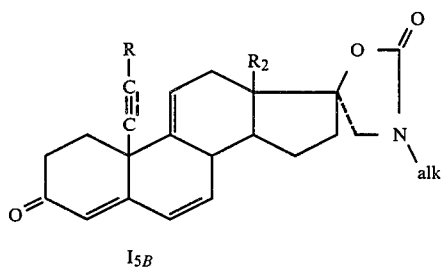

$I_{5B}$

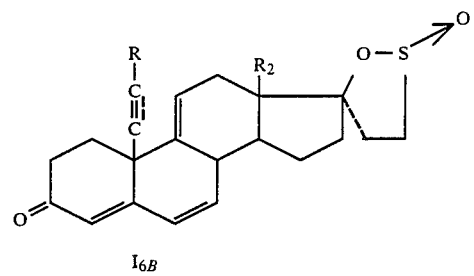

$I_{6B}$ which products are optionally treated either with an organomagnesium compound of the formula $R_1MgX'$ possibly in the presence of a copper salt wherein $R_1$ has the significance above and $X'$ is halogen or with an organometallic compound of the formula $(R_1)_2$ CuLi then with an acid, to obtain the products of the formulae

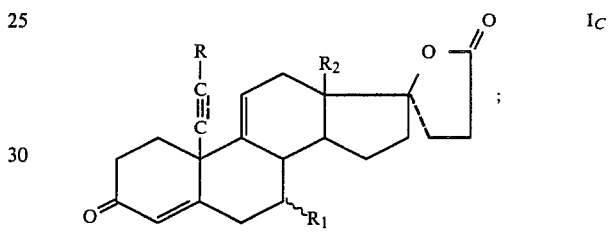

$I_C$

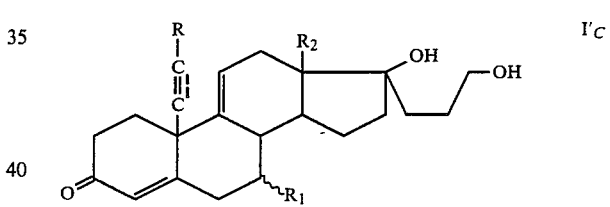

$I'_C$

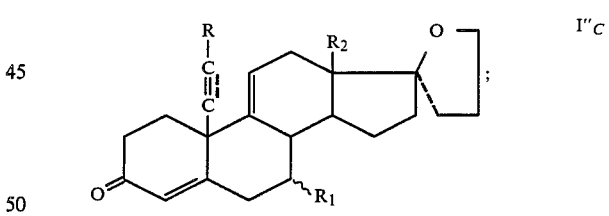

$I''_C$

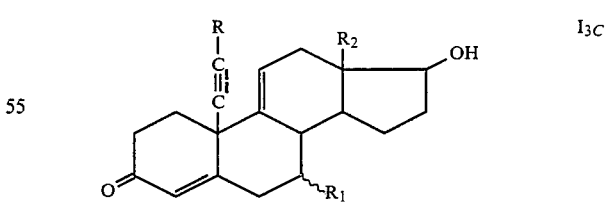

$I_{3C}$

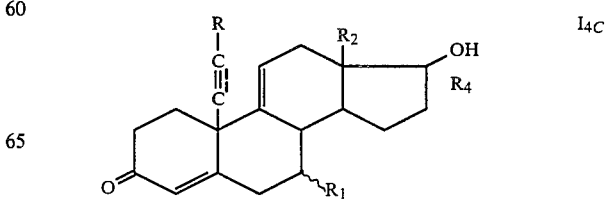

$I_{4C}$

I5C 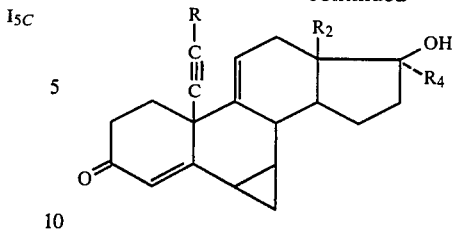

I6C 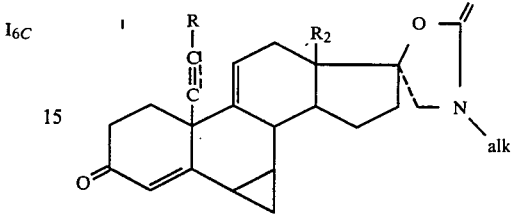

in the form of a mixture of 7α- and 7β-isomers which mixture is optionally separated and optionally the 7β products are submitted to a dehydrogenation reagent to obtain the corresponding $\Delta^{6(7)}$ products or the products of formulae $I_B$, $I_B'$, $I_B''$, $I_{3B}$, $I_{4B}$, $I_{5B}$ and $I_{6B}$ are reacted with a member chosen from the group consisting of trimethylsulfonium iodide and trimethylsulfoxonium iodide in the presence of a strong base to obtain the products of the formulae:

$I_D$ 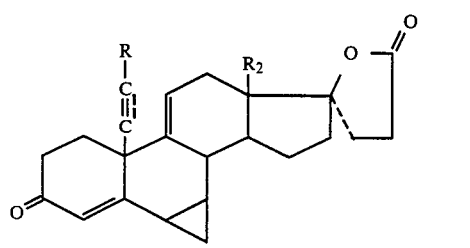

$I'_D$ 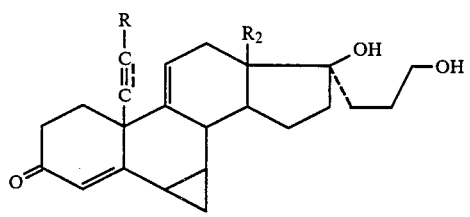

$I''_D$ 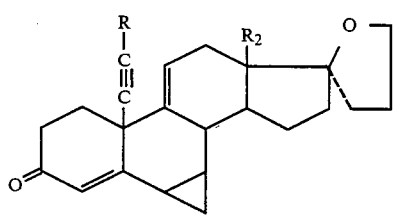

$I_{3D}$ 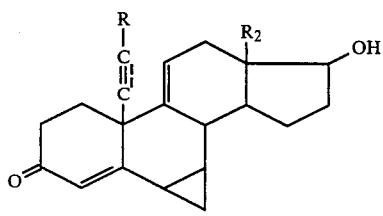

$I_{4D}$ 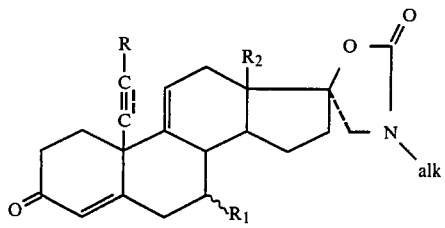

$I_{5D}$ 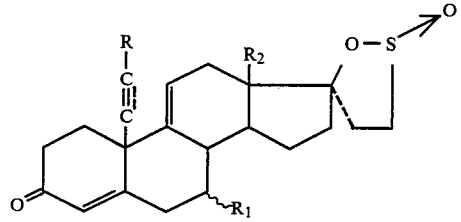

$I_{6D}$ 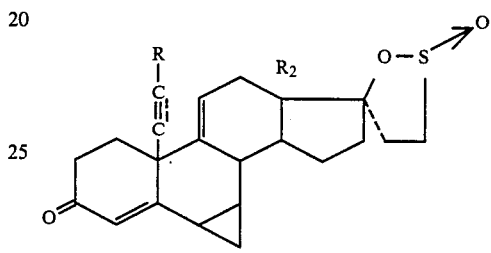

in the form of a mixture of 6α, 7α and 6β, 7β and optionally the isomers thus obtained are separated and optionally the products of formulae $I_4$, $I_B'$, $I_4''$, $I_{3A}$, $I_{4A}$, $I_B$, $I_B'$, $I_B''$, $I_{3B}$, $I_{4B}$, $I_C$, $I_C'$, $I_C''$, $I_{3C}$, $I_{4C}$, $I_D$, $I_D'$ $I_D''$, $I_{3D}$, $I_{4D}$ are treated with a dehydrogenation reagent or by a micro-organism able to dehydrogenate the molecule at position 1(2) to obtain the corresponding products including an unsaturation at position 1(2) and optionally the products of formulae $I_A$, $I_B$, $I_C$ and $I_D$ and the corresponding products having an unsaturation at position 1(2) are reacted with an alkali metal hydroxide or ammonia to obtain the corresponding products in which X is hydroxyl and Y is —CH₂CH₂CO₂M' in which M' is alkali metal or ammonium and optionally, the products thus obtained are reacted with an acid agent to obtain the products in which X is hydroxyl and Y is —CH₂CH₂CO₂H, and optionally, the products in which the substituent at position 10 is a R of hydroxyalkyl, are reacted with a carbon tetrabromide or tetrachloride in the presence of triphenylphosphine to obtain the corresponding bromine and chlorine derivatives, and optionally the products in which the substituent at position 10 includes a triple bond are reacted with a selective hydrogenation agent to obtain the corresponding products in which the substituent at position 10 includes a double bond, and optionally the products having an ethynyl at position 10 are reacted with a halosuccinimide to obtain the corresponding products having a —C≡C—Hal at position 10, and optionally the 17β-ol of the products having a 17α-hydrogen, R₄ or —CH₂—CH₂—CH₂OH, is acylated or etherified.

The protective groups of the functions when R is hydroxy or amino are selected from among the known groups. The protective group of the ketone designated K is preferably a ketal, thioketal, an oxime or an alkoxime. A ketal such as bismethoxy or a cyclic ketal such as ethylenedioxy is preferably used and these groups are eliminated in acid medium.

The trimethylsulfonium halide which is used is preferably iodide and the strong base in the presence of which the reaction is done is preferably potassium tert-butylate. The metallic derivative of acetonitrile can be for example the lithium derivative prepared in the presence of butyllithium and the derivative thus obtained which includes a 17-cyanoethyl is then subjected to the action of a base which can be for example sodium or potassium hydroxide and the product obtained is acidified, preferably by hydrochloride acid.

The reaction of allyl tetraalkyl phosphorodiamidate, preferably tetramethyl, with the product of formula II is carried out by the method described by STURTZ et al, Synthesis, 1980, p. 289. The strong base in the presence of which the reaction is effected is preferably butyllithium. The operation can also be effected in the presence of diazabicyclooctane (DABCO) or crowned ether and the product is then acidified, preferably with hydrochloric acid.

The action of the product of the formula XMg-CH$_2$CH$_2$CH$_2$OB with the product of formula II is carried out by the usual methods for preparing magnesian. B can be a usual protective group of hydroxyl such as tetrahydropyrannyl or tert.-butyl. B can also be a magnesium salt such as MgCl. The preparation and the use of such a group is described by CAHIEZ et al, Tetr. lett. No. 33 (1978), p. 3013. The product is acidified with an acid, preferably hydrochloric acid.

The conversion of products of formula I$_A$' into products of formula I$_A$" is carried out preferably in the presence of tosyl chloride and an amine base such as pyridine. The reduction of the products of formula II into products of formula I$_{3A}$ is carried out by usual methods, for example a hydride such as sodium borohydride can be used. The hydrolysis of the protective group K is carried out by the usual methods in an acid medium, for example, by the addition of hydrochloric acid.

The addition of the magnesian compound XMgR$_4$ and the reaction with (R$_4$)$_2$CuLi are carried out by the usual methods, for example operating in an anhydrous solvent such as tetrahydrofuran or ether and at a temperature lower than ambient. As for the other reactions indicated previously, an acid such as hydrochloric acid is then made to react to regenerate the ketone function at position 3.

The strong base used in the cyclization leading to product I$_{5A}$ is preferably potassium hydroxide in methanol. The acid in the presence of which the reaction with amine is carried out is preferably p-toluene sulfonic acid. The trimethylsulfonium halide is preferably an iodide and the strong base used is sodium or potassium hydroxide or potassium tert.-butylate. The separation of the diastereoisomers is carried out by the usual means of chromatography and crystallization.

The action of an orthoformate on the products I$_A$, I$_A$', I$_A$", I$_{3A}$, I$_{4A}$, I$_{5A}$ and I$_{6A}$ is intended to prepare the 3-alkoxy Δ$^{3,5}$ products with the formulae:

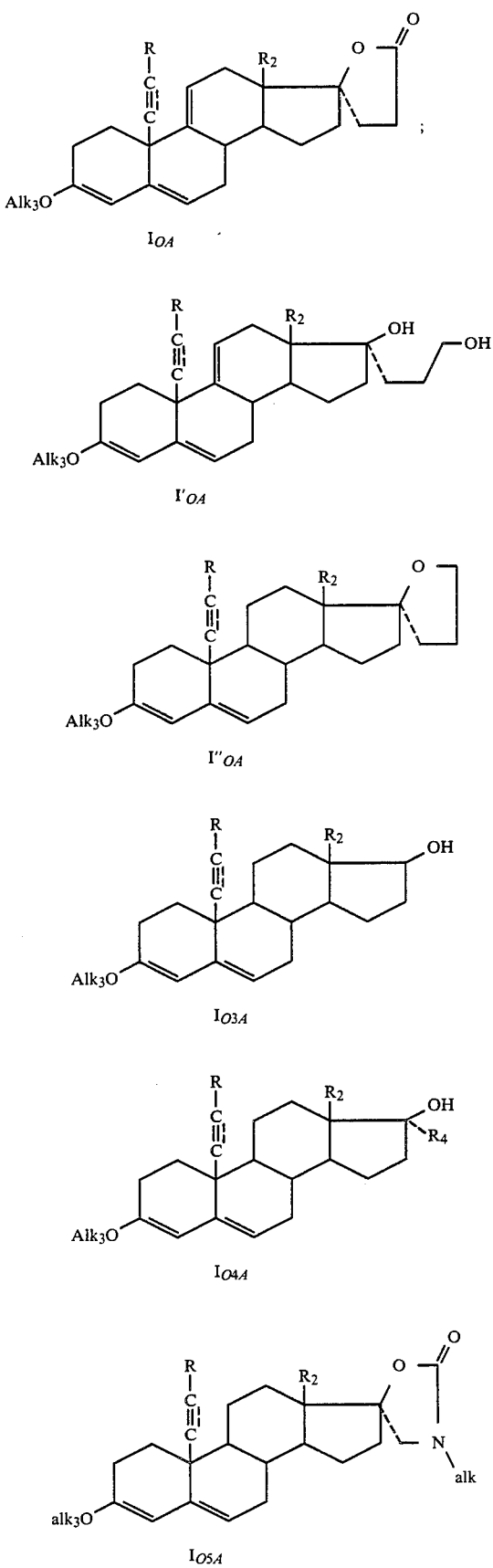

-continued

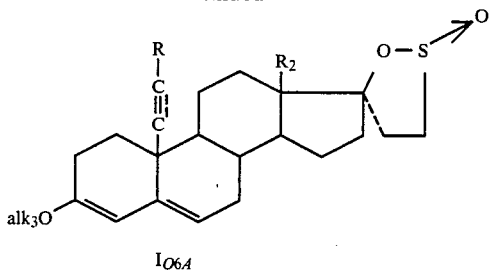

$I_{O6A}$

In the formulae $I_{OA}$, $I_{OA}'$, $I_{OA}''$, $I_{O3A}$, $I_{O4A}$, $I_{O5A}$ and $I_{O6A}$, R, $R_2$ and $R_4$ have the previous significance and $Alk_3$ is alkyl of 1 to 4 carbon atoms. The orthoformate used is preferably ethyl orthoformate in the presence of p-toluene sulfonic acid. The dehydrogenation agent is preferably chloranil (tetrachloro 1,4-benzoquinone). There can also be used DDQ (2,3-dichlor-5,6-dicyano-1,4-benzoquinone). The action of the product of the formula $R_1MgX'$ in which $X'$ is chlorine, bromine or iodine is carried out preferably in the presence of a cupric salt such as cupric acetate, chloride, bromide or a cuprous salt such as cuprous chloride, bromide or iodide.

The acid which is used after the reaction of a product of the formula $(R_1)_2CuLi$ is hydrochloric acid, nitric acid or sulfuric acid. The possible separation of different isomers is carried out by chromatography or fractional crystallization. The possible dehydrogenation of the 7β-products is carried out under the conditions stated previously. The base used to form the ylid corresponding to the trimethylsulfonium iodide and the trimethylsulfoxonium iodide is sodium hydride or potassium tert-.butylate. The possible separation is carried out according to the usual methods stated above.

The conversion of the products $I_A$ to $I_{6A}$, $I_B$ to $I_{6B}$, $I_C$ to $I_{6C}$ and $I_D$ to $I_{6D}$ into products having an unsaturation at position 1(2) is carried out preferably by a biochemical route using the bacteria "Arthrobacter simplex" but there can also be used other micro-organisms. In this case, the reaction is preferably carried out in a buffered aqueous medium. The chemical route can also be used by subjecting the products to the action of a derivative of p-benzoquinone or chloranil with the reaction taking place, for example, in solution in an organic solvent such as dioxane, acetone, benzene or tert.-butyl alcohol. There can also be used as dehydrogenation agent selenious anhydride or selenic benzene.

The alkali metal hydroxide to which the products of formulae $I_A$, $I_B$ and $I_C$ as well as the corresponding products having an unsaturation at position 1(2) are possibly subjected is preferably sodium or potassium hydroxide. The acid agent to which the products thus obtained are optionally subjected is hydrochloric acid, sulfuric acid, nitric acid or acetic acid.

The selective hydrogenation agent to which the products having at position 10 a substituent having a triple bond are optionally subjected is preferably hydrogen in the presence of a catalyst such as Lindlar's catalyst. The halosuccinimide which is reacted with the products having a 10-ethynyl is N-bromo- or N-chlorosuccinimide and the operation is preferably effected in the presence of silver nitrate.

The possible acylation of the products having a 17α-ol and a 17β hydrogen or $R_4$ is carried out by the usual methods. For example, an anhydride or an acyl halide such as acetic anhydride or acetyl chloride can be used.

The etherification of the same products is also carried out under usual conditions for example with an alkyl halide.

The products of formula II used as starting materials of the process of the application can be prepared by (1) either reacting a lithium compound of the formula $R'$—C≡C—Li with a product of the formula

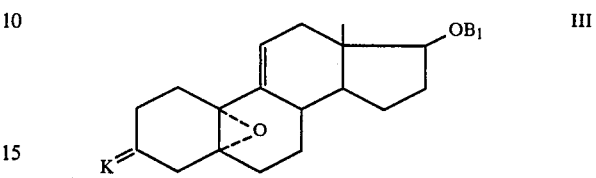

wherein $B_1$ is a protective group of hydroxyl to obtain a product of the formula

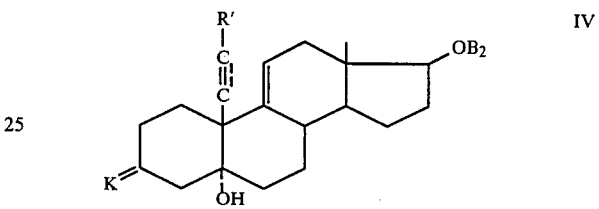

wherein $B_2$ is hydrogen or $B_1$ which product is subjected first to a deprotection reaction of the hydroxyl if the protective group has not been cleaved during the previous reaction, then to an oxidation reaction to obtain the products of formula II; (2) or by reacting a magnesian compound of the formula $R'$—C≡C—MgX with a product of the formula

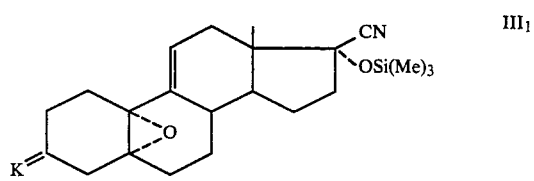

to obtain a product of the formula

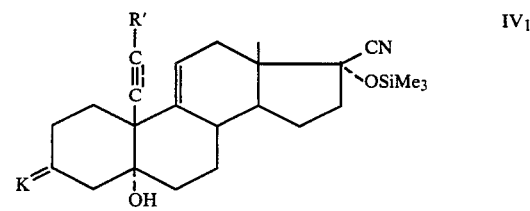

which product after alkaline hydrolysis gives the product of formula II.

The protective group which $B_1$ can be is preferably an acyl such as benzoyl and the lithium compound $R'$—C≡C—Li can be prepared by the usual methods. Hydrolysis of $B_1$ is also realized by the usual methods if the cleavage has not already occured during the previous reaction and can be effected in a basic medium. The oxidation at the 17 position is carried out for example by the use of pyridinium chlorochromate prepared according to Tet. Letters., No. 31 (1975), p. 2647. Such a preparation example is described in Example 5 of European Pat. No. 0,023,856.

The action of the magnesian compound of the formula R'—C≡C—MgX on the product of formula III, is carried out under the usual conditions. When the dotted line is a third bond between the carbons, the magnesian compound can be prepared in situ by reaction of R'—C≡C—H on a magnesian compound such as ethylmagnesium bromide. The operation is effected in a solvent such as tetrahydrofuran or ethyl ether and hydrolysis of the product of formula IV$_1$ is carried out under the usual conditions. Examples of such preparations appear in the experimental part.

Products of formulae III and III$_1$ are either known, for example by the French Pat. No. 2,377,417, or can be prepared by known methods starting from known products.

Product of formula I as defined above as well as 10β-ethynyl-17β-hydroxyΔ$^{4,9(11)}$ estradiene-3-one and 10β-ethynyl-17β-acetoxyΔ$^{4,9(11)}$ estradiene-3-one, this group constituting the general formula I'.

The novel compositions of the invention for inducing aldosterone antagonistic activity comprises an effective amount of at least one compound of formula I' and an inert pharmaceutical carrier or excipient. The said compositions also increase hydrosodium diuresis while preserving organic potassium. The compositions may be in the form of tablets, dragees, cachets, capsules, granules, emulsion, syrups, suppositories or injectable solutions or suspensions.

The compositions of the invention containing compounds of formula I' have the further advantage of possessing only slight hormonal side-effects. Tests carried out on the receptor site and in vivo have shown that the compounds of formula I' are less antiandrogenic than known antialdosteronic compounds and they are therefore useful for the treatment of arterial hypertension and cardiac deficiencies.

Examples of suitable excipients are talc, gum arabic, lactose, starch, magnesium, stearate, cocoa butter, aqueous and non-aqueous vehicles, fatty substances of animal or vegetable origin, paraffinic derivatives, glycols, various wetting agents, emulsifiers and dispersants and preservatives.

Among the preferred compositions of the invention are those wherein the active ingredient has the formula

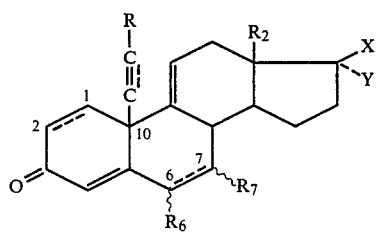

I' wherein R is selected from the group consisting of hydrogen, alkyl and substituted alkyl of 1 to 8 carbon atoms, alkenyl, substituted alkenyl, alkynyl and substituted alkynyl of 2 to 8 carbon atoms, aryl and substituted aryl, aralkyl and substituted aralkyl, protected hydroxy, optionally esterified carboxy, —NH$_2$, protected amino, mono and di-alkyl amino of 1 to 4 alkyl carbon atoms, halogen and trialkylsilyl, R$_2$ is methyl or ethyl, R$_6$ and R$_7$ together with the carbon atoms to which they are attached from cyclopropyl or R$_6$ is hydrogen and R$_7$ is R$_1$, R$_1$ is selected from the group consisting of hydrogen, alkyl and substituted alkyl of 1 to 6 carbon atoms, acetylthio and alkenyl, substituted alkenyl, alkynyl and substituted alkynyl of 2 to 6 carbon atoms, X is optionally acylated or etherified hydroxyl and Y is selected from the group consisting of hydrogen, R$_4$, —CH$_2$—CH$_2$COOM and —CH$_2$—CH$_2$—CH$_2$OH, M is hydrogen, alkali metal or —NH$_4$ or X and Y together form a member of the group consisting of

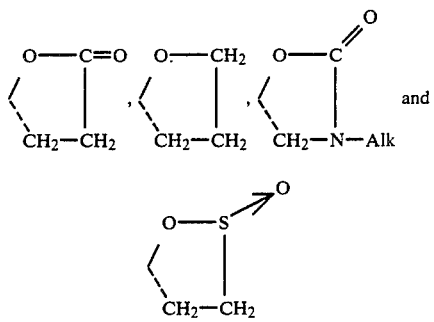

and or X is —OH and Y is

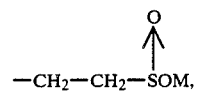

—CH$_2$—CH$_2$—SOM,

R$_4$ is selected from the group consisting of alkyl of 1 to 6 carbon atoms and alkenyl and alkynyl of 2 to 6 carbon atoms, Alk is alkyl of 1 to 8 carbon atoms, the dotted lines in the 1(2) and 6(7) indicate the optional presence of a second carbon-carbon bond with the proviso that when R$_6$ and R$_7$ form cyclopropyl, there is no 6(7) second bond, the dotted line in 10-substituent indicates the optional presence of a third carbon-carbon bond, the wavy lines at R$_6$ and R$_7$ indicate the possible α- or β-position.

Especially preferred are the compositions containing compounds of formula I' wherein R is selected from the group consisting of hydrogen, alkyl of 1 to 3 carbon atoms, phenyl and hydroxymethyl, R$_1$ is selected from the group consisting of hydrogen, alkyl of 1 to 4 carbon atoms and acetylthio and X is —OH and Y is either —CH$_2$—CH$_2$—COOM' wherein M' is hydrogen or alkali metal or hydrogen or X and Y form

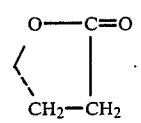

The most preferred compositions are those containing the γ-lactone of 10β-ethynyl-19-nor-17α-Δ$^{4,9(11)}$-pregnadiene-17β-ol-3-one-21-carboxylic acid and the γ-lactone of 10β-(-1-propynyl)-19-nor-17α-Δ$^{4,9(11)}$-pregnadiene-17β-ol-3-one-21-carboxylic acid and 10α-ethynyl-Δ$^{4,9(11)}$-estradiene-17β-ol-3-one.

The novel method of the invention of inducing aldosterone antagonistic activity in warm-blooded animals, including humans, comprises administering to warm-blooded animals an amount of at least one compound of formula I' sufficient to induce aldosterone antagonistic activity. The compounds may be administered orally, rectally, transcutaneously or intraveinously. The usual daily dose is 0.07 to 7 mg/kg depending on the compound, method of administration and the condition treated. For example, the product of Example 1 may be orally administered at a dose of 0.15 to 3 mg/kg.

The novel method of treating arterial hypertension and cardiac insufficiencies comprises administering to warm-blooded animals, including humans, an amount of a compound of formula I' sufficient to treat the same.

In the following examples there are described several preferred embodiments to illustrate the invention. However, it should be understood that the invention is not intended to be limited to the specific embodiments.

EXAMPLE 1

γ-lactone of 10β-ethynyl-19-nor-17α-$\Delta^{4,9(11)}$-pregnadiene-17β-ol-3-one-21-carboxylic acid

STEP A: (17S) 3,3-ethylenedioxy-10β-ethynyl-spiro[$\Delta^{9(11)}$-estrene-17,2'-oxiran]5α-ol Under agitation, a solution of 3.06 g of trimethylsulfonium iodide in 60 ml of dimethylsulfoxide was added to a suspension of 4.25 g of 3,3-ethylenedioxy-10β-ethynyl-5-$\Delta^{9(11)}$-estraen-5α-ol-17-one in 60 ml of tetrahydrofuran and 12 ml of a 2.4M solution of potassium tert.-butylate in tetrahydrofuran were added. After one hour of reaction, the reaction mixture was poured into water to which ammonium chloride had been added. After extracting with ethyl ether, the organic phase was washed and dried to obtain 4.5 g of the expected product after evaporation of the solvent under reduced pressure. The product was triturated in hexane and the crystals were separated and washed with hexane to obtain 3.895 g of (17S) 3,3-ethylenedioxy-10β-ethynyl-spiro[$\Delta^{9(11)}$-estrene-17,2'-oxiran]5α-ol melting at 142° C. After crystallization from ethanol, the product melted at 144° C.

Analysis: $C_{23}H_{30}O_4$; molecular weight=370.49. Calculated: %C, 74.56; %H, 8.16. Found: %C, 74.7; %H, 8.2.

STEP B: 3,3-ethylenedioxy-$\Delta^{9(11)}$-estraene-5α,17β-diol-17α-yl-3-propionitrile A solution of 11 ml of N-isopropyl-cyclohexyl amine in 60 ml of anhydrous tetrahydrofuran was cooled to −60° C. and a solution of 40 ml of n-butyl-lithium in hexane (titrating 15%) was added dropwise. Then, a solution of 3.5 ml of acetonitrile in 10 ml of anhydrous tetrahydrofuran was added to obtain a suspension which was stirred for 15 minutes at −5° to −10° C. After this, a solution of 4 g of the product of Step A in 20 ml of tetrahydrofuran was introduced and the mixture was rinsed with 5 ml of tetrahydrofuran, then allowed to react at ambient temperature for 20 hours, after which it was poured into a solution of ammonium chloride and extracted with ether. The organic phase was washed with water, dried to obtain 9 g of an oil after evaporation of the solvent.

The oil was chromatographed over silica and eluted with a mixture of cyclohexane and ethyl acetate (7-3) to separate 340 mg of the starting product, followed by 5 g of a product which was crystallized from ether at reflux. By cooling, separating and washing with ether, 2.827 g of 3,3-ethylenedioxy-$\Delta^{9(11)}$-estraene-5α,17β-diol-17α-yl-3-propionitrile melting at 200° C. were obtained By recrystallization from methylene chloride, an analysis sample was obtained melting at 203° C.

Analysis: $C_{25}H_{33}O_4N$; molecular weight=411.54. Calculated: %C, 72.96; %H, 8.08; %N, 3.4. Found: %C, 72.8; %H, 8.2; %N, 3.4.

STEP C: γ-lactone of 10β-ethynyl-19-nor-17α-$\Delta^{4,9(11)}$-pregnadiene-17β-ol-3-one-21-carboxylic acid A suspension of 1.9 g of the product of Step B in 30 ml of methanol was refluxed with 2 ml of 6N potassium hydroxide for 4 hours 30 minutes and then was cooled and acidified with 3 ml of concentrated hydrochloric acid. The mixture was diluted with 15 ml of methanol and refluxed for 90 minutes, after which it was cooled, diluted with water, and extracted with ethyl acetate. After washing, drying and evaporating the organic phase, 1.57 g of crude product were obtained. This product was chromatographed over silica and eluted with a mixture of cyclohexane and ethyl acetate (1-1) to obtain 1.225 g of γ-lactone of 10β-ethynyl-19-nor-17α-$\Delta^{4,9(11)}$-pregnadiene-17β-ol-3-one-21-carboxylic acid which was triturated in isopropyl ether and then separated to obtain 1.17 g of the product melting at 210° C.

EXAMPLE 2

Potassium 10β-ethynyl-$\Delta^{4,9(11)}$-estradiene-17β-ol-3-one-17α-propanoate

A suspension of 387 mg of the product of Example 1 in 4.3 ml of a 0.246N solution of potassium hydroxide in methanol and 4.3 ml of water was refluxed for 15 minutes and the solution obtained was distilled to dryness at 50° C. under reduced pressure. The traces of water were eliminated by two distillations with absolute ethanol and the moss obtained was dissolved in 2 ml of ethanol at 95° C. Ether (about 6 ml) was added slowly while scratching, then by cooling, separating, washing abundantly in ether and drying, 380 mg of potassium 10β-ethynyl-$\Delta^{4,9(11)}$-estradiene-17β-ol-3-one-17α-propanoiate melting at about 200° C. were obtained.

Analysis: $C_{23}H_{27}O_4K$; molecular weight=406.57. Calculated: %C, 61.22; %H, 7.13. Found: %C, 61.4; %H, 7.0.

EXAMPLE 3

γ-lactone of 10β-ethenyl-19-nor-17α-$\Delta^{4,9(11)}$-pregnadiene-17β-ol-3-one-21-carboxylic acid 180 mg of γ-lactone of 10β-ethynyl-19-nor-17α-$\Delta^{4,9(11)}$-pregnadiene-17β-ol-3-one-21-carboxylic acid (prepared in Example 1) were dissolved in 4 ml of ethyl acetate with 1 ml of pyridine, and 19 mg of Lindlar's catalyst were added with stirring in a hydrogenation atmosphere until the theoretical quantity of hydrogen had been absorbed, this is, about 25 minutes. The catalyst was filtered off and rinsed with ethyl acetate. The filtrate was diluted with water slightly acidulated with hydrochloric acid and the organic phase was decanted, washed with water, dried and concentrated to dryness under reduced pressure. The residue was chromatographed over silica impregnated with silver nitrate and elution with a mixture of ether and hexane (4-1) yielded 150 mg of γ-lactone of 10β-ethenyl-19-nor-17α-$\Delta^{4,9(11)}$-pregnadiene-17β-ol-3-one-21-carboxylic acid which was crystallized from isopropyl ether to obtain 121 mg

19 of the product melting at 144° C. and having a specific rotation of [α]_D: −57° (c=1% in CHCl_3).

EXAMPLE 4

γ-lactone of 10β-(1-propynyl)-19-nor-17α-Δ$^{4,9(11)}$-pregnadiene-17β-ol-3-one-21-carboxylic acid

STEP A:

3,3-ethylenedioxy-10β-(1-propynyl)-Δ$^{9(11)}$-estrene-5α-ol-17-one

In 25 ml of a 1M ethereal solution of ethyl magnesium bromidediluted with 25 ml of anhydrous tetrahydrofuran, methylacetylene was bubbled in for 1 hour at between 0° and 5° C. and then 2.15 g of 3,3-ethylenedioxy-5α,10α-epoxy-17α-trimethylsilyloxy-Δ$^{9(11)}$-estrene-17β-carbonitrile in 10 ml of tetrahydrofuran were added. The mixture was heated toi 40° C. for 2 hoiurs 30 minutes, and then left for 16 hours at ambient temperature. 20 ml of a solution of ammonium chloride were added at between 0° and 5° C. and then extraction with methylene chloride was effected. The extracts were washed with water, dried and concentrated to dryness. The residue was dissolved in 30 ml of ethanol and 3 ml of sodium hydroxide solution were added with stirring for 1 hour, followed by dilution with 90 ml of water. The mixture was extracted with chloroform and the organic phase was washed with water, dried and concentrated to dryness. The residue was crystallized from a mixture of methylene chloride and isopropyl ether to obtain 1.21 g of 3,3-ethylenedioxy-10β-(1-propynyl)-Δ$^{9(11)}$-estrene-5α-ol-17-one melting at 204° C.

STEP B: γ-lactone of 10β(1-propynyl)-19-nor-17α-Δ$^{4,9(11)}$-pregnadiene-17β-ol-3-one-21-carboxylic acid Under nitrogen and at −50° C., a solution of 3.6 ml of allyl tetramethylphosphorodiamidate in 15 ml of tetrahydrofuran was added over 15 minutes to a 1.6M solution of 23 ml of butyllithium in hexane and 20 ml of anhydrous tetrahydrofuran. The solution was stirred for one hour at −30° C. and then 1.78 g of the product of Step A were added over 5 minutes. After 2 hours 20 minutes, 38 ml of 2N hydrochloric acid were introduced into the mixture with stirring for 30 minutes followed by extraction with chloroform. The organic phase was washed with water, dried and concentrated to dryness and the residue was dissolved in 30 ml of ethanol, 6 ml of 6N hydrochloric acid were added and the mixture was heated at about 50° C. for 75 minutes. Then, the ethanol was distilled off and after taking up the residue in methylene chloride, the solution was washed with water, dried and concentrated to dryness. The residue was chromatographed over silica and eluted with a mixture of petroleum ether (b.p. 60°–80° C.) and ethyl acetate (1-1) to obtain 920 mg of γ-lactone of 10β-(1-propynyl)-19-nor-17α-Δ$^{4,9(11)}$-pregnadiene-17β-ol-3-one-21-carboxylic acid. The latter was taken up again with 2 ml of methylene chloride, filtered and 10 ml of isopropyl ether were added. The mixture was concentrated until crystals formed, cooled and separated. After drying, 790 mg of the said product were obtained melting at 200° C. and having a specific rotation of [α]_D: +32° (c=1% in CHCl_3).

EXAMPLE 5

γ-lactone of 10β-(phenylethynyl)-19-nor-17α-Δ$^{4,9(11)}$-pregnadiene-17β-ol-3-one-21-carboxylic acid

STEP A:

3,3-ethylenedioxy-10β-(phenylethynyl)-17α-trimethylsilyloxy-Δ$^{9(11)}$-estrene-5α-ol-17β-carbonitrile Into 50 ml of an M ethereal solution of ethyl magnesium bromide, 8 ml of phenylacetylene were added dropwise and then the mixture was diluted with 35 ml of anhydrous tetrahydrofuran and left for one hour at ambient temperature. Then, 6.45 g of 5α,10β-epoxy-17α-trimethylsilyloxy-Δ$^{9(11)}$-estrene-3-one-17β-carbonitrile were added, and the mixture was stirred for 4 hours at ambient temperature and then was heated for 1 hour at 35° C. The reaction mixture was cooled and poured into a solution of ammonium chloride and was extracted with ethyl acetate. The extracts were washed with water, dried and concentrated to dryness to obtain 8.9 g of product. The residue was chromatographed over silica and eluted with a mixture of cyclohexane and ethyl acetate (9-1) to obtain 4.6 g of 3,3-ethylenedioxy-10β-(phenylethynyl)-17α-trimethylsiloxy-Δ$^{9(11)}$-estrene-5α-ol-17β-carbonitrile which was crystallized from hexane to obtain 3.47 g of the said product melting at 176° C.

STEP B: B 3,3-ethylenedioxy-10β-(phenylethynyl)-Δ$^{9(11)}$-estrene-5α-ol-17-one 3.1 g of the product of Step A were stirred in 31 ml of ethanol and 3.1 ml of sodium hydroxide and then 10 ml of ethanol were added. Stirring was continued for 2 hours and after dilution with 100 ml of water, the mixture was filtered and the product was washed with water and dried to obtain 2.49 g of 3,3-ethylenedioxy-10β-(phenylethynyl)-Δ$^{9(11)}$-estrene-5α-ol-17-one melting at 199° C.

STEP C: γ-lactone of 10β-(phenylethynyl)-19-nor-17α-Δ$^{4,9(11)}$-pregnadiene-17β-ol-3-one-21-carboxylic acid 10 ml of a 1.6M solution of n-butyl-lithium in hexane were cooled to −70° C. and were diluted with 10 ml of anhydrous tetrahydrofuran. Then, at −70° C. 1.6 ml of allyl N,N,N',N'-tetramethylphosphorodiamidate in 10 ml of tetrahydrofuran were added dropwise and the mixture was left to react for 1 hour at −10° C. 865 mg of the product of Step B were added followed by stirring for 15 hours at ambient temperature and the mixture was acidified by adding 10 ml of 2N hydrochloric acid and 1 ml of concentrated hydrochloric acid and stirring for 30 minutes. After extraction with ethyl acetate, the organic phase was washed with water, dried and concentrated to dryness under reduced pressure. 25 ml of methanol were added to the residue and 5 ml of 6N hydrochloric acid were added and the mixture was heated at 50° C. for one hour. After cooling, dilution with water, extraction with ethyl acetate, the organic phase was washed with water, dried and concentrated to dryness under reduced pressure. The residue was chromatographed over silica and eluted with a mixture of cyclohexane and ethyl acetate (1-) to obtain 540 mg of γ-lactone of 10β-(phenylethynyl)-19-nor-17α-Δ$^{4,9(11)}$-pregnadiene-17β-ol-3-one-21-carboxylic acid.

EXAMPLE 6

γ-lactone of
10β-[3-hydroxy-prop-1-yny]3-oxo-19-nor-17α-Δ$^{4,9(11)}$-pregnadiene-17β-ol-21-carboxylic acid

STEP A:
3,3-ethylenedioxy-10β-[3-(2RS-tetrahydropyrannyl-oxy)-prop-1-ynyl]-methylsiloxy-Δ$^{9(11)}$-estrene-5α-ol-17β-carbonitrile 4.4 ml of 3-(2-tetrahydropyrannyloxy)-1-propyne in 15 ml of anhydrous ether were added dropwise into 30 ml of a 0.9M ethereal solution of propyl magnesium chloride. The mixture was diluted with 20 ml of tetrahydrofuran and was stirred for 50 minutes at ambient temperature. 1.32 g of 3,3-ethylenedioxy-5α,10α-epoxy-17α-trimethylsilyloxy-Δ$^{9(11)}$-estrene-17β-carbonitrile were introduced with stirring for 5 hours at ambient temperature and the mixture was heated for 1 hour at 35° C. and then poured into a dilute solution of monosodium phosphate. The mixture was extracted with ethyl acetate and the extracts were washed with water, dried and concentrated to dryness. The residue was chromatographed over silica and eluted with a mixture of petroleum ether and ethyl acetate (4-1) to obtain 1.335 g of 3,3-ethylenedioxy-10β-[3-(2RS-tetrahydropyrannyloxy)-prop-1-ynyl]-methylsilyloxy-Δ$^{9(11)}$-estrene-5α-ol-17β-carbonitrile.

STEP B:
3,3-ethylenedioxy-10β-[3-(2-RS-tetrahydropyrannyloxy)-prop-1-ynyl]-Δ$^{9(11)}$-estrene-5α-ol-17-one 1,330 g of the product of Step A were dissolved in 60 ml of methanol and 3 ml of sodium hydroxide were added and reaction was allowed for 2 hours. After dilution with 200 ml of water, crystallization was initiated. The crystals were separated, washed with water and dried to obtain 900 mg of 3,3-ethylenedioxy-10β-[3-(RS-tetrahydropyrannyloxy)-prop-1-ynyl]-Δ$^{9(11)}$-estrene-5α-ol-17-one melting at 143° C.

STEP C: γ-lactone of
3,3-ethylenedioxy-10β-[3-(2RS-tetrahydropyrannyloxy)-prop-1-ynyl]-19-nor-17α-Δ$^{9(11)}$-pregnaene-5α,17β-diol-21-carboxylic acid To 12.5 ml of a 1.6M solution of butyllithium in hexane cooled to −50° C., 12.5 ml of anhydrous tetrahydrofuran were added, and then, at −65° C. 2.2 ml of a solution of allyl tetramethylphosphorotriamidate in 8 ml of dry tetrahydrofuran were added. The mixture was adjusted to −10° to −15° C. and left to react for one hour. 890 mg of the product of Step B were added, and the mixture was left to stand for 18 hours at ambient temperature. After dilution with water, extraction with ethyl acetate, washing with water, drying and concentrating to dryness, the residue was chromatographed over silica. Elution with a mixture of benzene and ethyl acetate (7-3) yielded 560 mg of γ-lactone of 3,3-ethylenedioxy-10β-[3-(2RS-tetrahydropyrannyloxy)-prop-1-ynyl]-19-nor-17α-Δ$^{9(11)}$-pregnaene-5α,17β-diol-21-carboxylix acid.

STEP D: γ-lactone of
10β-[3-hydroxy-prop-1-ynyl]-19-nor-17α-Δ$^{4,9(11)}$-pregnadiene-17β-ol-3-one-21-carboxylic acid 555 mg of the product of Step C were dissolved in 10 ml of methanol and 5 ml of 6N hydrochloric acid and the mixture stood for 18 hours at ambient temperature, then for 1 hour at 60° C. After cooling, diluting with water and extracting with methylene chloride, the extract was washed with water, dried and concentrated to dryness under reduced pressure. The residue was chromatographed over silica and eluted with a mixture of cyclohexane and ethyl acetate (1-1) to obtain 350 mg of γ-lactone of 10β-[3-hydroxy-prop-1-ynyl]-19-nor-17α-Δ$^{4,9(11)}$-pregnadiene-17β-ol-3-one-21 carboxylic acid which after crystallization from ethyl acetate melted at 198° C. and had a specific rotation of $[\alpha]_D = +31° \pm 1°$ (c=1%, CHCl$_3$).

EXAMPLE 7

γ-lactone of
10β-ethynyl-19-nor-17α-Δ$^{4,6,9(11)}$-pregnatriene-17β-ol-3-one-21-carboxylic acid

STEP A: γ-lactone of
3-ethoxy-10β-ethynyl-19-nor-17α-Δ$^{3,5,9(11)}$-pregnatriene-17β-ol-21-carboxylic acid To a solution of 6.77 g of the product of Example 1 in 68 ml of dioxane, 20 ml of ethyl orthoformate and then 203 mg of monohydrate p-toluene sulfonic acid were added with stirring under nitrogen. After 2 hours 30 minutes, 0.6 ml of triethylamine were added and the mixture was poured into 60 ml of a saturated aqueous solution of sodium bicarbonate. The product was extracted with methylene chloride, and 12.35 g of crude product were obtained which were chromatographed over silica. Elution with cyclohexane-ethyl acetate (7-3) and triethylamine 1 o/oo yielded 6.1 g of γ-lactone of 3-ethoxy-10β-ethynyl-19-nor-17α-Δ$^{3,5,9(11)}$-pregnatriene-17β-ol-21-carboxylic acid melting at 196° C.

STEP B: γ-lactone of
10β-ethynyl-19-nor-17α-Δ$^{4,6,9(11)}$-pregnatriene-17β-ol-3-one-21-carboxylic acid 2.164 g of chloranil were added with stirring to a solution of 2.164 g of the product of Step A in 43 ml of acetone containing 5% of water. After stirring for 22 hours at ambient temperature, the reaction mixture was poured into 100 ml of a mixture of water saturated with sodium bicarbonate and water with 10% of sodium thiosulfate (1-1). After extraction with methylene chloride and washing with water, drying and evaporating to dryness, 2.1 g of residue were obtained which were chromatographed over silica. Elution with methylene chloride-acetone 4-1 yielded 1.947 g of a crystallized product which was triturated in 10 ml of ethyl ether. After filtering, washing with ethyl ether and drying under vacuum, 1.847 g of a product were isolated which were then dissolved in a mixture of ethanol and methylene chloride. The methylene chloride was evaporated, and after cooling, filtering, washing with ethanol and drying, 1.751 g of γ-lactone of 10β-ethynyl-19-nor-17α-Δ$^{4,6,9(11)}$-pregnatriene-17β-ol-3-one-21-carboxylic acid were obtained with a specific rotation of $[\alpha]_D = 243.5° \pm 4.5°$ (c=0.5%, CHCl$_3$).

Analysis: C$_{23}$H$_{24}$O$_3$. Calculated: %C, 79.28; %H, 6.94. Found: %C 79.2; 7.0.

EXAMPLE 8

γ-lactone of
7α-(acetylthio)-10β-ethynyl-19-nor-17α-Δ$^{4,9(11)}$-pregnadiene-17β-ol-3-one-21-carboxylic acid A mixture of 1.7 g of the product of Example 7, 85 ml of acetic acid, 3.4 ml of concentrated hydrochloric acid and 0.85 ml of thioacetic acid was stirred for 24 hours at ambient temperature under nitrogen and the mixture was poured into a saturated aqueous solution of sodium bicarbonate and was extracted with ethyl acetate. The extracts were washed with water and evaporated to dryness. The 2 g of a resin were chromatographed over silica and eluted with cyclohexane-ethyl acetate 3-2 to obtain 753 mg of amorphous γ-lactone of 7α-(acetylthio)-10β-ethynyl-19-nor-17α-Δ$^{4,9(11)}$-pregnadiene-17β-ol-3-one-21-carboxylic acid.

Analysis: $C_{25}H_{28}O_5S$. Calculated: %C, 70.72; %H, 6.64; %S, 7.55. Found: %C, 70.5; %H, 6.7; %S, 7.3.

EXAMPLE 9

γ-lactone of
10β-ethynyl-7α-propyl-19-nor-17α-Δ$^{4,9(11)}$-pregnadiene-17β-ol-3-one-21-carboxylic acid A solution of 2.7 ml of n-propyl bromide in 2.7 ml of tetrahydrofuran was added under nitrogen to a mixture of 900 g of magnesium and 27 ml of tetrahydrofuran with stirring for one night at ambient temperature to obtain propylmagnesium bromide.

To 14 ml of the preceding magnesium solution, a solution of 1.514 g of cuprous iodide, 0.69 g of lithium bromide in 3.7 ml of tetrahydrofuran were added over 30 minutes under nitrogen at −40° C. The mixture was rinsed with 1 ml of tetrahydrofuran and the suspension was stirred for 15 minutes at −40° C., then cooled to −70° C. and over 10 minutes, 1.05 ml of boron trifluoride etherate were added.

After stirring for 20 minutes at −70° C., over 35 minutes a solution of 923 mg of γ-lactone of 10β-ethynyl-19-nor-17α-Δ$^{4,6,9(11)}$-pregnatriene-17β-ol-3-one-21 carboxylic acid of Example 7 in 50 ml of tetrahydrofuran was added, followed by rinsing twice with 5 ml of tetrahydrofuran while stirring at −70° C. After 45 minutes, 4 ml of 5N hydrochloric acid were added and the temperature was allowed to rise to the ambient. Stirring was continued for 3 hours and then, after dilution with water saturated with sodium chloride, the mixture was extracted with ethyl acetate. The organic phase was washed with dilute ammonia, then with distilled water, dried and evaporated to dryness under vacuum. The residue was chromatographed over silica and eluted with cyclohexane-ethyl acetate 7-3 to obtain 480 mg of γ-lactone of 10β-ethynyl-7α-propyl-19-nor-17α-Δ$^{4,9(11)}$-pregnadiene-17β-ol-3-one-21-carboxylic acid. The product was dissolved in a mixture of methylene chloride and isopropyl ether and the methylene chloride was distilled off to obtain 460 mg of product melting at 148° C. and having a specific rotation of $[α]_D = +40° ±1°$ (c=0.8% in ethanol).

Analysis: $C_{26}H_{32}O_3$; molecular weight=392.5. Calculated: %C, 79.55; %H 8.21. Found: %C, 79.6; %H, 8.3.

During the chromatography, there was also isolated 247 mg of the less mobile 7β-isomer, which was recrystallized in the same way from a mixture of methylene chloride-isopropyl ether to obtain 121 mg of the said product melting at 147° C. and having a specific rotation of $[α]_D = −14° ±2°$ (c=0.5% in ethanol).

EXAMPLE 10

γ-lactone of
10β-(1-propynyl)-19-nor-17α-Δ$^{4,6,9(11)}$-pregnatriene-17β-ol-3-one-21-carboxylic acid

STEP A: γ-lactone of
3-ethoxy-10β-(1-propynyl)-19-nor-17α-Δ$^{3,5,9(11)}$-pregnatriene-17β-ol-21-carboxylic acid A mixture of 20.3 g of γ-lactone of 10β-(1-propynyl)-19-nor-17α-δ$^{4,9(11)}$-pregnadiene-17β-ol-3-one-21-carboxylic acid of Example 7 in 200 ml of dioxane, 60 ml of ethyl orthoformate and 0.6 g of monohydrate p-toluene sulfonic acid was stirred at ambient temperature for 4 hours and after adding 2 ml of triethylamine, the mixture was poured slowly into 200 ml of a solution of sodium bicarbonate. The precipitation was extracted with dichloromethane and the 31.1 g of product obtained were then dissolved in 100 ml of dichloromethane. To this solution, there was added slowly 250 ml of isopropyl ether followed by cooling. 5.8 g of crystals of γ-lactone of 3-ethoxy-10β-(1-propynyl)-19-nor-17α-Δ$^{3,5,9(11)}$-pregnatriene-17β-ol-21-carboxylic acid melting at 210° C. were obtained and the mother liquors were concentrated. The residue was purified by chromatography and elution with cyclohexane-ethyl acetate 7-3 to obtain 13.2 mg of the said product melting at 210° C.

STEP B: γ-lactone of
10β-(1-propynyl)-19-nor-17α-Δ$^{4,6,9(11)}$-pregnatriene-17β-ol-3-one-21-carboxylic acid A mixture of 5.8 g of the product of Step A, 116 ml of acetone containing 5% of water 5.8 g of chloranil was stirred at ambient temperature for 22 hours and was poured into a mixture of 150 g of a 10% solution of sodium bicarbonate in water and 150 g of sodium thiosulfate solution.

After extraction with dichloromethane, the solvent was evaporated to obtain 6.9 g of residue which was purified by chromatography over silica. Elution with ethyl acetate and petroleum ether 1-1 yielded 5.1 g of γ-lactone of 10β-(1-propynyl)-19-nor-17α-Δ$^{4,6,9(11)}$-pregnatriene-17β-ol-3-one-21-carboxylic acid which was crystallized by dissolving in 20 ml of dichloromethane and adding 200 ml of isopropyl oxide to obtain 4.77 g of crystals melting at 248° C.

EXAMPLE 11

γ-lactone-10β-(1-butynyl)-19-nor-17α-Δ$^{4,9(11)}$-pregnadiene-17β-ol-3-one-21-carboxylic acid

STEP A:
10β-(but-1-ynyl)-3,3-(ethylenedioxy)-Δ$^{9(11)}$-estrene-5α-ol-17-one Ethylacetylene was bubbled for 2½ hours into a mixture of 330 ml of ethyl magnesium bromide in a 0.5N ethereal solution and 330 ml of tetrahydrofuran and then 10 g of 3,3-ethylenedioxy-5α,10α-epxoy-17α-trimethylsilyloxy-Δ$^{9(11)}$-estrene-17β-carbonitrile were introduced all at once. The mixture was heated at 40°–50° C. for 4 hours 30 minutes and then was brought back to ambient temperature and poured into a mixture of ammonium chloride and ice. After decanting, the organic phase was washed with water, extracted with chloroform, dried and evaporated to dryness, 12 g of residue were obtained which were dissolved in 100 ml of ethanol at 95° C. 10 ml of sodium hydroxide were added with stirring for 45 minutes. Then, the ethanol was distilled off and the residue were taken up in chloroform. The solution was washed with water, dried and evaporated to dryness to obtain 9.3 g of residue. The latter was chromatographed over silica and eluted with petroleum ether-ethyl acetate (1-1) with 1 o/oo of triethylamine to obtain 4.6 g of product with an Rf=0.35. The product was dissolved in 10 ml of methylene chloride and filtered and 30 ml of isopropyl ether were added. After cooling, filtering and drying at 50° C., 240 mg of 10$\beta$-(but-1-ynyl)-3,3-(ethylenedioxy)-$\Delta^{9(11)}$-estrene-5$\alpha$-ol-17-one melting at 139° C. were obtained.

Analysis: $C_{24}H_{32}O_4$; molecular weight=384.52. Calculated: %C, 74.97; %H, 8.39. Found: %C, 75.0; %H, 8.5.

STEP B: $\gamma$-lactone of 10$\beta$-(1-butynyl)-19-nor-17$\alpha$-$\Delta^{4,9(11)}$-pregnadiene-17$\beta$-ol-3-one-21-carboxylic acid 24 ml of tetrahydrofuran were added at −50° C. to 24 ml of a 1.65M solution of n-butyl-lithium in hexane and then, over 15 minutes and at −40° C. a solution of 4 ml of allyl tetramethylphosphorodiamidate in 16 ml of tetrahydrofuran were added. After stirring for 1 hour at −30° C., 1.92 g of the product of Step A in solution in 20 ml of tetrahydrofuran were added. The mixture was allowed to rise to ambient temperature and after stirring for 2 hours, 40 ml of 2N hydrochloric acid were added at between 0° and +5° C. followed by stirring for 30 minutes. The mixture was extracted with chloroform and the organic phase was washed with water, dried and evaporated to dryness. The 3 g of residue were dissolved in 30 ml of ethanol, and 6 ml of 0.5N hydrochloric acid were added under nitrogen with heating to 50° C. for two hours. After evaporation to dryness, the residue was taken up in methylene chloride and the solution was washed with water and evaporated to dryness. The 2 g of residue were chromatographed over silica and eluted with petroleum ether and ethyl acetate 1-1 to obtain 1.26 g of product with an Rf=0.22. The latter was dissolved in 20 ml of isopropyl ether at reflux and after concentrating to one half, crystallization was initiated, followed by cooling, filtering, washing with iced isopropyl ether and drying at 50° C. under vacuum to obtain 880 mg of $\gamma$-lactone of 10$\beta$-(1-butynyl)-19-nor-17$\alpha$-$\Delta^{4,9(11)}$-pregnadiene-17$\beta$-ol-3-one-21-carboxylic acid which was crystallized by dissolving it in 8 ml of isopropyl ether at reflux, filtering, concentrating until turbidity appeared, initiating crystallization hot, cooling, filtering, washing with petroleum ether and then drying at 50° C. under vacuum to obtain 770 mg of product melting at 94° C. and having a specific rotation of $[\alpha]_D$=+35° ±1° (c=1% chloroform).

Analysis: $C_{25}H_{30}O_3$; molecular weight=378.48. Calculated: %C 79.33; %H 7.99. Found: %C, 79.5; %H, 8.2.

EXAMPLE 12

$\gamma$-lactone of 10$\beta$-(1-pentynyl)-19-nor-17$\alpha$-$\Delta^{4,9(11)}$-pregnadiene-17$\beta$-ol-3-one-21-carboxylic acid STEP A: 3,3-(ethylenedioxy)-10$\beta$-(1-pentynyl)-$\Delta^{9(11)}$-estrene-5$\alpha$-ol-17-one Using the procedure of Step A of Example 11, 6.45 g of 3,3-ethylenedioxy-5$\alpha$,10$\alpha$-epoxy-17$\alpha$-trimethylsilyoxy-$\Delta^{9(11)}$-estrene-17$\beta$-carbonitrile were reacted to obtain after chromatography 2.61 g of 3,3-(ethylenedioxy)-10$\beta$-(1-pentynyl)-$\Delta^{9(11)}$-estrene-5$\alpha$-ol-17-one. Crystallization of 200 mg of the product from 2 ml of isopropyl ether at reflux gave 140 mg of the pure product smelting at 120° C.

Analysis: $C_{25}H_{30}O_4$; molecular weight=398.56. Calculated: %C 75.34; %H 8.6 Found: %C, 75.1; %H, 8.7.

STEP B: $\gamma$-lactone of 10$\beta$-(1-pentynyl)-19-nor-17$\alpha$-$\Delta^{4,9(11)}$-pregnadiene-17$\beta$-ol-3-one-21-carboxylic acid Using the procedure of Step B of Example 11, 2 g of the product of Step A were reacted to obtain after chromatography 1.13 g of $\gamma$-lactone of 10$\beta$-(1-pentynyl)-19-nor-17$\alpha$-$\Delta^{4,9(11)}$-pregnadiene-17$\beta$-ol-3-one-21-carboxylic acid which was crystallized by dissolving in 2 ml of methylene chloride and adding 10 ml of isopropyl ether to obtain 970 mg of pure product and then 910 mg after a second crystallization melting at 123° C. and having a specific rotation of $[\alpha]_D$=+41° ±1° (c=1% chloroform).

Analysis: $C_{26}H_{32}O_3$; molecular weight=392.52. Calculated: %C, 79.55; %H, 8.22. Found: %C, 79.6; %H, 8.3.

EXAMPLE 13

10$\beta$-(but-1-ynyl)-$\Delta^{4,9(11)}$-estradiene-17$\beta$-ol-3-one 385 mg of sodium borohydride were added to a solution of 770 mg of 10$\beta$-(but-1-ynyl)-3,3-(ethylenedioxy)-$\Delta^{9(11)}$-estrene-5$\alpha$-ol-17-one of Step A of Example 11 in 15 ml of ethanol and after stirring for 45 minutes, the mixture was distilled to dryness under vacuum. The residue was taken up in methylene chloride and the solution was washed with water, dried and evaporated to dryness to obtain 770 mg of product melting at 195° C.

The 770 mg of product obtained above were dissolved under nitrogen at 50°-60° C. in 15 ml of ethanol and 0.8 ml of 0.5N hydrochloric acid were added, followed by heating for 4 hours. The mixture was evaporated to dryness and the residue was taken up in methylene chloride. The solution was washed with water, dried and evaporated to dryness to obtain 750 mg of resin. The latter was chromatographed over silica and eluted with petroleum ether-ethyl acetate 1-1 to obtain 630 mg of product with an Rf=0.33. The latter was crystallized by dissolving in 6 ml of isopropyl ether at a reflux, then filtering, concentrating to a half, initiating crystallization, cooling, separating, washing with iced isopropyl ether and drying to obtain 485 mg of 10$\beta$-(but-1-ynyl)-$\Delta^{4,9(11)}$-estradiene-17$\beta$-ol-3-one melting at 95° C. and having a specific rotation of $[\alpha]_D$=+136° ±2° (c=1% in chloroform).

EXAMPLE 14

10$\beta$-(pent-1-ynyl)-$\Delta^{4,9(11)}$-estradiene-17$\beta$-ol-3-one

Using the procedure of Example 13, 570 mg of 10$\beta$-(pent-1-ynyl)-3,3-(ethylenedioxy)-$\Delta^{9(11)}$-estrene-5$\alpha$-ol-17-one of Step A of Example 12 were reacted to obtain 280 mg of 10$\beta$-(pent-1-ynyl)-$\Delta^{4,9(11)}$-estradiene-17$\beta$-ol-3-one having a specific rotation of $[\alpha]_D$=+134° ±2° (c=1% in chloroform).

EXAMPLE 15

10β-(prop-1-ynyl)-Δ$^{4,9(11)}$-estradiene-17β-ol-3-one

Using the procedure of Example 13, 520 mg of 10β-(prop-1-ynyl)-3,3-(ethylenedioxy)-Δ$^{9(11)}$-estrene-5α-ol-17-one of Step A of Example 4 were reacted to obtain 260 mg of 10β-(prop-1-ynyl)-Δ$^{4,9(11)}$-estradiene-17β-ol-3-one melting at 154° C. and having a specific rotation of $[\alpha]_D = 130° \pm 1°$ (c=1% of chloroform).

EXAMPLE 16

γ-lactone of
7α-propyl-10β-(1-propynyl)-19-nor-17α-Δ$^{4,9(11)}$-pregnadiene-17β-ol-3-one-21-carboxylic acid Using the procedure of Example 9, the product of Example 10 was reacted to obtain γ-lactone of 7α-propyl-10β-(1-propynyl)-19-nor-17α-Δ$^{4,9(11)}$-pregnadiene-17β-ol-3-one-21-carboxylic acid melting at 110° C. and having Rf=0.2 (eluent: cyclohexaneethyl acetate, 7-3).

Analysis: $C_{27}H_{34}O_5$. Calculated: %C 79.77; %H, 8.43. Found: %C, 76.6; %H, 8.5.

EXAMPLE 17

γ-lactone of
7α-acetylthio-10β-(1-propynyl)-19-nor-17α-Δ$^{4,9(11)}$-pregnadiene-17β-ol-3-one-21-carboxylic acid Using the procedure of Example 8, the product of Example 10 was reacted to obtain γ-lactone of 7α-acetylthio-10β-(1-propynyl)-19-nor-17α-Δ$^{4,9(11)}$-pregnadiene-17β-ol-3-one-21-carboxylic acid with an Rf=0.1 (eluent: dichloromethane-acetone 9-2).

Analysis: $C_{26}H_{30}SO_4$; molecular weight=458.59. Calculated: %C 71.20; %H, 6.89; %S, 7.31. Found: %C, 71; %H, 6.8; %S, 7.2.

EXAMPLE 18

10β-(3-hydroxy-1-propynyl)-Δ$^{4,9(11)}$-estradiene-17β-ol-3-one 58 mg of sodium borohydride were added to a solution cooled to +5° of 290 mg of 3,3-ethylenedioxy-10β-[3-(2RS-tetrahydropyrannyloxy)-1-propynyl]-Δ$^{9(11)}$-estrene-5α-ol-17-one of Example 6, Step B and 6 ml of methanol. After standing 2 hours with stirring, diluting with water, extracting with methylene chloride and concentrating to dryness, 300 mg of product were obtained. The product was taken up in 6 ml of methanol and 3 ml of 0.5N hydrochloric acid were added with stirring for 1 hour. After dilution with water, initiating crystallization, separating and drying, 166 mg of 10β-(3-hydroxy-1-propynyl)-Δ$^{4,9(11)}$-estradiene-17β-ol-3-one were obtained melting at 204° C. after crystallization from a mixture of methylene chloride and isopropyl ether and with a specific rotation of $[\alpha]_D = +124°$ (c=1%, chloroform).

EXAMPLE 19

γ-lactone of
10β-(1-propynyl)-19-nor-17α-Δ$^{1,4,9(11)}$-pregnatriene-17β-ol-3-one-21-carboxylic acid 2 g of the product of Example 4 suspended in 20 ml of toluene were heated for 20 hours at reflux in the presence of 3.2 g of phenylseleninic anhydride and was then allowed to cool. The mixture was poured into a solution of sodium bicarbonate and was extracted with ethyl acetate. The extracts were washed with an aqueous solution of sodium hydroxide, dried, and the solvents were evaporated under reduced pressure. The residue was chromatographed over silica and eluted with methylene chloride-acetone (97-3) to obtain 0.511 g of γ-lactone of 10β-(1-propynyl)-19-nor-17β-Δ$^{1,4,9(11)}$-pregnatriene-17β-ol-3-one-21-carboxylic acid.

IR Spectrum (chloroform) 1764 cm$^{-1}$: α-lactone; 1667 cm$^{-1}$; conjugated ketone 1631-1608 cm$^{-1}$; —C≡C—.

EXAMPLE 20

γ-lactone of
7α-methyl-10β-(1-propynyl)-19-nor-17α-Δ$^{4,9(11)}$-pregnadiene-17β-ol-3-one-21-carboxylic acid 75 mg of cupric chloride and 24 mg of lithium chloride were mixed together in 55 ml of tetrahydrofuran and, under an inert atmosphere, 2 g of the product of Example 10 were added. The mixture was cooled to +2°/+4° C. and then, over 2 hours, 7.9 ml of a 1.05M ethereal solution of methyl magnesium iodide were added dropwise. The mixture was stirred for 2 hours and while maintaining the temperature at +20° C., 9 ml of 5N hydrochloric acid were added. The temperature was allowed to return to the ambient and extraction was effected with ethyl acetate. The extracts were washed with water, then with an aqueous solution of ammonium hydroxide and then with water, dried and concentrated to dryness. After chromatography over silica and elution with cyclohexane-ethyl acetate 8.5-1.5, 384 mg of γ-lactone of 7α-methyl-10β-(1-propynyl)-19-nor-17α-Δ$^{4,9(11)}$-pregnadiene-17β-ol-3-one-21-carboxylic acid melting at 125° C., and 550 mg of the 7β isomer of the product were obtained.

Analysis: $C_{25}H_{30}O_3$; molecular weight=378.52. Isomer 7α: Calculated: %C, 79.33; %H, 7.99. Found: %C, 79.0; %H, 8.1. Isomer 7β: Calculated: %C, 79.33; %H, 7.99. Found: %C, 79.3; %H, 8.0.

EXAMPLE 21

γ-lactone of (Z)
10β-(1-propenyl)-19-nor-17α-Δ$^{4,9(11)}$-pregnadiene-17β-ol-3-one-21-carboxylic acid 8 ml of pyridine and then 0.29 g of Lindar's catalyst were added to a solution of 1.45 g of the product of Example 4 in 32 ml of ethyl acetate. After hydrogenation of 2 hours, the catalyst was filtered and the pyridine was eliminated by washing with 2N hydrochloric acid. The organic phase was decanted, washed with water, dried and concentrated to dryness. The residue was taken up in ether, heated to reflux, cooled and the crystals were separated and dried to obtain 840 mg of γ-lactone of (Z) 10β-(1-propenyl)-19-nor-17α-Δ$^{4,9(11)}$-pregnadiene-17β-ol-3-one-21-carboxylic acid melting at 170° C. after crystallization from a mixture of methylene chloride and isopropyl ether and having a specific rotation of $[\alpha]_D = 47°$ (c=1% chloroform).

Analysis: $C_{24}H_{30}O_3$: molecular weight=366.51. Calculated: %C, 78.65; %H, 8.25. Found: %C, 78.4; %H, 8.4.

EXAMPLE 22

γ-lactone of
10β-(3-chloro-1-propynyl)-19-nor-17α-Δ$^{4,9(11)}$-pregnadien-17β-ol-3-one-21-carboxylic acid 1 g of triphenylphosphine was added to a solution of 0.5 g of the product of Example 6 in 5 ml of tetrahydrofuran and 5 ml of carbon tetrachloride. After heating for 30 minutes at 80° C. with stirring, the mixture was concentrated to dryness under reduced pressure. The residue was chromatographed over silica and eluted with cyclohexane-ethyl acetate 9-1 then 7-3. The product was chromatographed over silica and eluted with ether to obtain 0.38 g of γ-lactone of 10β-(3-chloropropynyl)-19-nor-17α-Δ$^{4,9(11)}$-pregnadien-17β-ol-3-one-21-carboxylic acid melting at 134° C. after crystallization from a mixture of methylene chloride and isopropyl ether and having a specific rotation of $[α]_D$ = +17.5° (c=1% chloroform).

Analysis: $C_{24}H_{27}O_3Cl$: molecular weight=398.93. Calculated: %C, 72.26; %H, 6.82; %Cl, 8.88. Found: %C, 72.1; %H, 6.8; %Cl, 9.2.

EXAMPLE 23

(6α,7α,17α)γ-lactone of 6,7-dihydro-10β-(1-propynyl)-3'H-cyclopropa-(6,7)-19-nor-Δ$^{4,9(11)}$-pregnadien-17β-ol-3-one-21-carboxylic acid Into 4.04 g of trimethylsulfoxonium iodide in solution in 15 ml of dimethylsulfoxide, 8.6 ml of potassium tert.-butylate in solution in 8.2 ml of tetrahydrofuran were added under an inert atmosphere and after stirring for 15 minutes, a solution of 2.737 g of the product of Example 10 in 3 ml of tetrahydrofuran was added. The mixture was heated to 59° to 60° C. for one hour and was then cooled, and 8 ml of N hydrochloric acid were added. The mixture was diluted with a saturated aqueous solution of sodium chloride and was extractd with ethyl acetate. The organic phase was washed with a saturated aqueous solution of sodium bicarbonate, and then with a saturated aqueous solution of sodium chloride. After drying, concentrating to dryness, and purifying by chromatography over silica and elution with cyclohexane-ethyl acetate 6-4, 1.28 g of (6α,7α,17α)γ-lactone of 6,7-dihydro-10β-(1-propynyl)-3'H-cyclopropa-(6,7,)-19-nor-Δ$^{4,9(11)}$-pregnadien-17β-ol-3-one-21-carboxylic acid were obtained melting at 243° C. after crystallization from isopropanol and having a specific rotation of $[α]_D$ = −276° (c=0.5% CHCl$_3$).

Analysis: Calculated: %C, 79.75; %H, 7.49. Found: %C, 79.4; ;1 %H, 7.6.

EXAMPLE 24

13β-ethyl-10β-ethynyl-Δ$^{4,9(11)}$-gonadien-17β-ol-3-one

STEP A: 13β-ethyl-3,3-ethylenedioxy-10β-ethynyl-Δ$^{9(11)}$-gonene-5α,17β-diol 3.9 g of 3,3-ethylenedioxy-5α,10α-epoxy-13β-ethyl-Δ$^{9(11)}$-gonene-17β-ol [prepared as in French Pat. No. 2,377,417] were dissolved in benzene and the solution was concentrated under reduced pressure. The residue was taken up in 40 ml of ethylene diamine and under an inert atmosphere, 3.6 g of acetylene complex of lithium ethylene diamine were added. The mixture was heated to 45° C. and stirred for 24 hours. A further 3.9 g of the complex were added with stirring for 72 hours at 48° C. The mixture was cooled and poured into a solution of ammonium chloride. After extracting with ethyl acetate, the organic phase was washed with water, dried and the solvents were expelled undeer reduced pressure. The residue was chromatographed over silica and eluted with cyclohexane hexane ethyl-acetate 1-1 to obtain 2.3 g of 13β-ethyl-10β-ethynyl-Δ$^{4,9(11)}$-gonadien-17β-ol-3-one.

STEP B: 13β-ethyl-10β-ethynyl-Δ$^{5,9(11)}$-gonadien-17β-ol-3-one 3.5 ml of 0.5N hydrochloric acid were added to 0.7 g of the product of Step A in 7 ml of methanol and after heating at 55° C. for 1 hour, the mixture was diluted with water and extracted with methylene chloride. The organic phase was washed with water, dried and concentrated to dryness under reduced pressure. The residue was chromatographed over silica and eluted with cyclohexane-ethyl acetate (1-1). The product was purified by a further chromatography over silica and elution with ether-hexane 6-4 to obtain 0.39 g of 13β-ethyl-10β-ethynyl-Δ$^{5,9(11)}$-gonadien-17β-ol-3-one melting at 120° C. after crystallization from isopropyl ether and having a specific rotation of $[α]_D$ = +98.5° (c=1% chloroform).

Analysis: $C_{21}H_{26}O_2$: molecular weight=310.44. Calculated: %C, 81.25; %H, 8.44. Found: %C, 81.1; %H, 8.7.

EXAMPLE 25

γ-lactone of 13β-ethyl-10β-ethynyl-18,19-dinor-(17α)-$^{4,9(11)}$-pregnadien-17β-ol-3-one-21-carboxylic acid STEP A: 17β-ethyl-10β-ethynyl-3,3-ethylenedioxy-Δ$^{9(11)}$-gonen-5α-ol-17-one 2.4 g of pyridinium dichromate were added to a solution cooled to +4° C. of 0.75 g of the product of Step A of Example 24 in 12 ml of dimethylformamide and after stirring for 90 minutes, the mixture was diluted with water and extracted with ether. The organic phase was washed with water, dried and concentrated to dryness to obtain 0.74 g of 17β-ethyl-10β-ethynyl-3,3-ethylenedioxy-Δ$^{9(11)}$-gonen-5α-ol-17-one.

STEP B: γ-lactone of 13β-ethyl-10β-ethynyl-18,19-dinor-(17α)-$^{4,9(11)}$-pregnadien-17β-ol-3-one-21-carboxylic acid Using the procedure of Step B of Example 4, 0.95 g of the product of Step A were reacted for 65 hours at ambient temperature and the reaction medium was poured into a solution of ammonium chloride and extracted with etjyl acetate. The organic phase was washed with water, dried and concentrated to dryness under reduced pressure. The residue was taken up in 19 ml of methanol and 9 ml of 0.5N hydrochloric acid were added. The mixture was heated for 90 minutes at 50°–55° C. and was then cooled and diluted with water, and extracted with methylene chloride. The crude product was purified by chromatography over silica and elution with ether-ethyl acetate, 8.5-1.5 to obtain 0.26 g of γ-lactone of 13β-ethyl-10β-ethynyl-18,19-dinor-(17α)-Δ$^{4,9(11)}$-pregnadien-17β-ol-3-one-21-carboxylic acid melting at 198° C. after crystallization from isopropyl ethyl and having a specific rotation of $[α]_D$ = +4° (c=1% chloroform).

Analysis: $C_{24}H_{28}O_3$: molecular weight=364.49. Calculated: %C, 79.08; %H, 7.74. Found: %C, 79.1; %H, 7.8.

EXAMPLE 26

10β-ethynyl-17α-methyl-Δ$^{4,9(11)}$-estradien-17β-ol-3-one

STEP A:
3,3-ethylenedioxy-10β-ethynyl-17α-methyl-Δ$^{9(11)}$-estrene-5α,17β-diol At −65° C. and over 15 minutes, 27 ml of a 1.8M solution of methyl lithium in ether were added to a suspension of 3.05 g of cubric iodide in 30 ml of tetrahydrofuran and after stirring for 15 minutes, a solution of 713 mg of 3,3-ethylenedioxy-10β-ethynyl-Δ$^{9(11)}$-estraen-5α-ol-17-one in 20 ml of tetrahydrofuran was added. The mixture was stirred for 2 hours at −65° C. and then was allowed to return to ambient temperature and was stirred for a further 39 hours. After cooling, saturated aqueous solution of ammonium chloride was added and extraction with ethyl acetate was effected. The organic phase was washed with water, dried and concentrated to drynes. The residue was chromatographed over silica and was eluted with cyclohexane-ethyl acetate 6-4 to obtain 560 mg of 3,3-ethylenedioxy-10β-ethynyl-17α-methyl-Δ$^{9(11)}$-estrene-5α,17β-diol.

STEP B:
10β-ethynyl-17αmethyl-Δ$^{4,9(11)}$-estradien-17β-ol-3-one

Under an inert atmosphere, 704 mg of the product of Step A were heated for 3 hours 15 minutes in 14 ml of ethanol and 3.5 of 5N hydrochloric acid. After cooling, 2 ml of ammonia were added amd the ethanol was evaporated under reduced pressure. The mixture was diluted with water and extraction with ethyl acetate was effected. The organic phase was washed with water, dried and concentrated to cryness. The residue was chromatographed over silica and was eluted with cyclohexane-ethyl acetate 6-4 to obtain 472 mg of 10β-ethynyl-17α-methyl-Δ$^{4,9(11)}$-estradien-17β-ol-3-one melting at 174° C. after crystallization from ethyl ether and having a specific rotation of $[\alpha]_D = +65.5°\pm2°$ (c=0.5% chloroform).

Analysis: Calculated: %C, 81.24; %H, 8.44. Found: %C, 81.2; %H, 8.3.

EXAMPLE 27

10β-ethynyl-17α-ethyl-Δ$^{4,9(11)}$-estradien-17β-ol-3-one

STEP A:
3,3-ethylenedioxy-10β-ethynul-17α-ethyl-Δ$^{9(11)}$-estrene-5α,17β-diol 100 mg of cuprous bromide were added to 40 ml of a 0.5M solution of methyl magnesium bromide cooled to +10° C. and ater stirring for 20 minutes, 1 g of the product of Step A of Example 1 was added and stirring was maintained for 2 hours 30 minutes. By pouring into a saturated aqueous solution of ammonium chloride at 0° C., extracting with methylene chloride and concentrating the extracts to dryness, 1.04 g of 3,3-ethylenedioxy-10β-ethynyl-17α-ethyl-Δ$^{9(11)}$-estrene-5α,17β-diol were obtained.

STEP B:
10β-ethynyl-17α-ethyl-Δ$^{4,9(11)}$-estradien-17β-ol-3-one

A mixture of 971 mg of the product of Step A in 20 ml of ethanol and 10 ml of 2N hydrochloric acid was stirred for 16 hours at ambient temperature and then for 3 hours at 40° C. followed by cooling. The mixture was neutralized with ammonia and extracted with methylene chloride. The solvent was evaporated and the residue was chromatographed over silica. Elution with hexane-ethyl acetate 6-4 yielded after crystallization from ethyl ether, 372 mg of 10β-ethynyl-17α-ethyl-Δ$^{4,9(11)}$-estradien-17β-ol-3one melting at 147°–148° C. and having a specific rotation of $[\alpha]_D = +56°\pm5°$ (c=0.2% in chloroform).

EXAMPLE 28

10β-ethynyl-17α-propyl-Δ$^{4,9(11)}$-estradien-17β-ol-3-one

STEP A:
3,3-ethylenedioxy-10β-ethynyl-17α-propyl-Δ$^{9(11)}$-estraene-5α,17β-diol Using the procedure of Step A of Example 27, 465 mg of cuprous bromide, 90 ml of a 0.7M solution in tetrahydrofuran of ethyl ammonium bromide and 4.650 g of the product of Step A of Example 1 were reacted to obtain after extraction with ethyl acetate and purification by chromatography over silica and elution with cyclohexane—ethyl acetate 4.375 g of 3,3-ethylenedioxy-10β-ethynyl-17α-propyl-Δ$^{9(11)}$-estraene-5α,17β-diol.

STEP B:
10β-ethynyl-17α-butyl-Δ$^{4,9\ (11)}$-estradien-17β-ol-3-one 21 ml of 5N hydrochloric acid were added to a solution of 4.2 g of the product of Step A in 130 ml of ethanol, and the mixture was heated for 150 minutes at about 55° C. with stirring under an inert atmospher. The mixture was partially concentrated, diluted with ethyl acetate, washed with water, cried and concentrated to dryness. The residue was chromatographed over silica and was eluted with a mixture of hyclohexane and ethyl acetate 8-2 to obtain 2-8 g of 10β-ethynyl-17α-propyl-Δ$^{4,9(11)}$-estradien-17β-ol-3-one melting at 167° C, after crystallization from isopropanol and having a specific rotation of $[\alpha]_D = +58.5°\pm2.5°$ (c=0.5% in chloroform).

EXAMPLE 29

10β-ethynyl-17α-butyl-Δ$^{4,9}$(11)-estradien-17β-ol-3-one

STEP A:
3,3-ethylenedioxy-10β-ethynyl-17α-butyl-Δ$^{9(11)}$-estrene-5α,17β-diol 100 mg of cuprous bromide in 18 ml of a solution of n-propyl magnesium bromide in tetrahydrofuran was stirred for 30 minutes at +7° C. and 1 g of the product of Step A of Example 1 in solution in 10 ml of tetrahydrofuran were added. After allowing the temperature to return to the ambient and stirring for 45 minutes, the mixture was poured into an iced saturated aqueous solution of ammonium chloride and was extracted with ethyl acetate. The organic phase was washed with water, then with a saturated aqueous solution of sodium chloride and concentrated to dryness. The residue was purified by chromatography over silica and elution with cyclohexane-ethyl acetate 6-4 with 1 o/oo of triethylamine to obtain after crystallization from ether, 1 g of 3,3-ethylenedioxy-10β-ethynyl-17α-butyl-Δ$^{9(11)}$-estrene-5α,17β-diol melting at about 130° C.

STEP B:
10β-ethynyl-17α-butyl-Δ$^{4,9(11)}$-estradien-17β-ol-3-one 870 mg of the product of Step A in 26 ml of ethanol and 34 ml of 2N hydrochloric acid were stirred for 6 hours at 40° C. and then 16 hours at ambient temperature. The mixture was poured into iced water, alkalinized with concentrated ammonia, and extracted with ethyl acetate. The organic phase was washed with water, then with a saturated aqueous solution of sodium chloride, dried and concentrated to dryness. The residue was chromatographed over silica and eluted with cyclohexane-ethyl acetate 6-4 to obtain after crystallization from isopropyl ether, 554 mg of 10β-ethynyl-17α-butyl-Δ$^{4,9(11)}$-estradien-17β-ol-3-one melting at 134° C. and having a specific rotation of $[α]_D = +45.5° ±2°$ (c=0.5% chloroform).

Analysis: Calculated: %C, 81.77; %H, 9.15. Found: %C, 82.0; %H, 9.2.

EXAMPLE 30

10β-ethynyl-17α-(2-propen-1-yl)-Δ$^{4,9(11)}$-estradien-17β-ol-3-one

STEP A:

3,3-ethylenedioxy-10β-ethynyl-17α-(2-propen-1-yl)-Δ$^{9(11)}$-estrene-5α,17β-diol A solution of 1 g of 3,3-ethylenedioxy-10β-ethynyl-Δ$^{9(11)}$-estren-5α-ol-17-one and 8 ml of tetrahydrofuran was introduced over 10 minutes into 15.6 ml of a 0.9M solution of allyl ammonium chloride with stirring for 4 hours. The mixture was then poured into a saturated aqueous solution of ammonium chloride at 0° C., and was extracted with methylene chloride. After evaporating the solvent and purifying by chromatography over silica and elution with hexane-ethyl acetate 1-1 with 1% of triethylamine, 987 mg of 3,3-ethylenedioxy-10β-ethynyl-17α-(2-propen-1-yl)-Δ$^{9(11)}$-estrene-5α,17β-diol were obtained.

STEP B:

10β-ethynyl-17β-hydroxy-17α-(2-propen-1-yl)-estra-4,9(11)-dien-3-one 940 mg of the product obtained in the preceding stage A is agitated for 2 hours at ambient temperature and then 3 hours at 50° C. in 20 cm³ of ethanol and 5 cm³ of 5M hydrochloric acid. After cooling, neutralizing with ammonia, extracting with methylene chloride and evaporating the solvent, the residue is chromatographed on silica (eluent: cyclohexane-ethyl acetate 7-3), and, after crystallizing from ethanol, 475 mg of the expected product is obtained melting at 150° C.

Analysis: $C_{23}H_{28}O_2$: molecular weight=336.477. Calculated: %C, 81.9; %H, 8.60. Found: %C, 82.1; %H, 8.39.

EXAMPLE 31

10β-ethynyl-17α-(3-hydroxypropyl)-Δ$^{4,9(11)}$-estradien-17β-ol-3-one

STEP A:

3,3-ethylenedioxy-10β-ethynyl-17α-[3-(1,1-dimethylethoxy)-propyl]-Δ$^{9(11)}$-estrene-5α,17β-diol Under an inert atmosphere, 16 g of magnesium in 200 ml of tetrahydrofuran were heated to 60° C. and a few drops of 1,2-dibromoethane were added. Then, over 30 minutes, 49.7 g of 3-(1,1-dimethylethoxy)-chloropropane in solution in 100 ml of tetrahydrofuran were added and the mixture was refluxed for 3 hours. 64 ml of the magnesium compound thus prepared in 64 ml of ethyl ether was refluxed under an inert atmosphere and then 4 g of 3,3-ethylenedioxy-10β-ethynyl-Δ$^{9(11)}$-estrene5α-ol-17-one were added. The mixture was refluxed for 42 hours while twice adding 96 ml of the magnesium compound and 96 ml of ethyl ether. The reaction medium was cooled and a saturated aqueous solution of ammonium chloride was added, followed by filtering and concentrating the filtrate to dryness. The residue was chromatographed over silica and eluted with cyclohexane-ethyl acetate 7-3 to obtain 2.87 g of 3,3-ethylenedioxy-10β-ethynyl-17α-[3-(1,1-dimethylethoxy)-propyl]-Δ$^{9(11)}$-estrene-5α,17β-diol.

STEP B:

10β-ethynyl-17α-[3-(1,1-dimethylethoxy)-propyl]-Δ$^{4,9(11)}$-estradien-17β-ol-3-one Using the procedure of Step B of Example 26, 1.5 g of the product of Step A in 45 ml of ethanol and 7.5 ml of 5N hydrochloric acid were reacted to obtain after purification by chromatography over silica and elution with cyclohexane-ethyl acetate 7-3 0.8 g of 10β-ethynyl-17α-[3,(1,1-dimethylethoxy)-propyl]-Δ$^{4,9(11)}$-estradien-17β-ol-3-one.

STEP C:

10β-ethynyl-17α-(3-hydroxypropyl)-Δ$^{4,9(11)}$-estradien-17β-ol-3-one

A solution of 100 mg of the product of Step B in 0.2 ml of dioxane and 0.3 ml of concentrated hydrochloric acid was stirred for 150 minutes at ambient temperature under an inert atmosphere and the reaction mixture was poured into a saturated aqueous solution of sodium bicarbonate and was extracted with ethyl acetate. The organic phase was washed with water, dried and concentrated to dryness under reduced pressure. The residue was chromatographed on silica and eluted with methylene chloride-methanol 95-5 to obtain 20 mg of 10β-ethynyl-17α-(3-hydroxypropyl)-Δ$^{4,9(11)}$-estradien-17β-ol-3-one melting at 144° C. after crystallization from isopropyl ether and then from 2,2-dimethoxypropane and having a specific rotation of $[α]_D = +36°5 ±2°$ (c=0.5% chloroform).

Analysis: Calculated: %C, 77.92; %H, 8.53. Found: %C, 77.8; %H, 8.7.

EXAMPLE 32

4′,5′-dihydro-10β-ethynyl-spiro-[Δ$^{4,9(11)}$-estradien-17,2′-(3H)-furan]-3-one Under an inert atmosphere and over a period of 5 minutes, 122 mg of tosyl chloride were added to a solution of 115 mg of product of Example 31 in 2.3 ml of pyridine followed by stirring for 15 hours at ambient temperature. The mixture was poured into water to which hydrochloric acid had been added and was extracted with ethyl acetate. The organic phase was washed with water, dried and concentrated to dryness to obtain 100 mg of residue which was purified by chromatography over silica. Elution with an 8-2 mixture cyclohexane-ethyl acetate yielded 4′,5′-dihydro-10β-ethynyl-spiro-[Δ$^{4,9(11)}$-estradien-17,2′-(3H)-furan]-3-one melting at 126° C. after crystallization from isopropyl ether and having a specific rotation of $[α]_D = +17° ±2°$ (c=0.5% in chloroform).

Analysis: Calculated: %C, 82.10; %H, 8.38. Found: %C, 82.3; %H, 8.6.

EXAMPLE 33

10β-ethynyl-17β-acetoxy-17α-(3-hydroxypropyl)-Δ$^{4,9(11)}$-estradien-3-one

STEP A:

10β-ethynyl-17β-acetoxy-17α-(3-acetoxypropyl)-Δ$^{4,9(11)}$-estradien-3-one

Under an inert atmosphere, 100 mg of the product of Step B of Example 32, 0.6 ml of acetic anhydride and 5 mg of p-toluene-sulfonic acid were stirred for 90 minutes and then was poured into ice and a saturated aqueous solution of sodium bicarbonate was added. The mixture was dried and concentrated to dryness under reduced pressure. The residual acetic acid was eliminated by entrainment with toluene and the residue was chromatographed over silica. Elution with methylene chloride-acetone 9-1 yielded 98 mg of 10β-ethynyl-17β-acetoxy-17α-(3-acetoxypropyl)-Δ$^{4,9(11)}$-estradien-3-one.

STEP B:

10β-ethynyl-17β-acetoxy-17α-(3-hydroxypropyl)-Δ$^{4,9(11)}$-estradien-3-one 70 mg of the product of Step B and 17 mg of potassium bicarbonate in 1 ml of methanol were heated to reflux under an inert atmosphere for one hour and then was poured into a mixture of water and ice and extracted with methylene chloride. The organic phase was washed with water, then with a saturated aqueous solution of sodium chloride, dried and concentrated to dryness under reduced pressure. The residue was chromatographed over silica and eluted with methylene chloride-methanol 95-5 to obtain 60 mg of 10β-ethynyl-17β-acetoxy-17α-(3-hydroxypropyl)-Δ$^{4,9(11)}$-estradien-3-one with a specific rotation of $[\alpha]_D = +10°\pm1°$ (c=1.2% in chloroform).

EXAMPLE 34

Potassium 10β-(1-propynyl)-19-nor-17α-Δ$^{4,9(11)}$-pregnadien-17βol-3-one-21-carboxylate Under an atmosphere of nitrogen, 1.69 g of the product of Example 4 in 21.2 ml of a 0.21N solution of potassium hydroxide in methanol and 21.2 ml of water was refluxed for 30 minutes and after concentrating to dryness at 50° C. under reduced pressure, traces of water were eliminated by entrainment with ethanol. The residue was taken up in ether, separated, washed with ether and dried under reduced pressure at 50° C. to obtain 1.92 g of crude product. 1.7 g of the residue were dissolved in 9 ml of warm ethanol and the solution was filtered. 80 ml of ether were added and crystallization was initiated. After standing at ambient temperature and then for 1 hour at +4° C., the crystallized product was separated and dried under reduced pressure at 50° C. to obtain 1.5 g of potassium 10α-(1-propynyl)-19-nor-17α-Δ$^{4,9(11)}$-pregnadien-17β-ol-3-one-21-carboxylate melting at 248° C. and having a specific rotation of $[\alpha]_D = +34°5\pm2°$ (c=0.5% ethanol).

EXAMPLE 35

10β-(1-propynyl)-17α-methyl-Δ$^{4,9(11)}$-estradien-17β-ol-3-one

STEP A:

3,3-ethylenedioxy-10β-(1-propynyl)-17α-methyl-Δ$^{9(11)}$-estrene-5α,17β-diol

Under an inert atmosphere, 370 mg of 3,3-ethylenedioxy-10β-(1-propynyl)-Δ$^{9(11)}$-estren-5α-ol-17-one of Step A of Example 4 in 4 ml of tetrahydrofuran were added dropwise to a 0.9M ethereal solution of magnesium methyl iodide. 10 ml of tetrahydrofuran were added and the mixture was stirred for 90 minutes at ambient temperature after which it was poured into iced ammonium chloride and extracted with ethyl chloride. The organic phase was washed with water, then with a saturated aqueous solution of sodium chloride, then dried and concentrated to dryness under reduced pressure. The residue was chromatographed over silica and eluted with cyclohexane-ethyl acetate 6-4 with 1 o/oo of triethylamine to obtain 281 mg of 3,3-ethylenedioxy-10β-(1-propynyl)-17α-methyl-Δ$^{9(11)}$-estrene-5α,17β-diol melting at 183° C.

STEP B:

10β-(1-propynyl)-17α-methyl-Δ$^{4,9(11)}$-estradien-17β-ol-3-one 596 mg of the product of Step A were heated to 50° C. for 90 minutes in 12 ml of ethanol and 3.2 ml of 5N hydrochloric acid and after returning to ambient temperature, the mixture was poured into iced water, alkalized with ammonia, then extracted with ethyl acetate. The organic phase was washed with water, then with a saturated aqueous solution of sodium chloride, dried and concentrated to dryness under reduced pressure. The residue was chromatographed over silica and eluted with n-hexane-ethyl acetate 6-4 to obtain 438 mg of 10β-(1-propynyl)-17α-methyl-Δ$^{4,9(11)}$-estradien-17β-ol-3-one melting at 130° C. after crystallization from ether and having a specific rotation of $[\alpha]_D + 95°\pm3°$ (c=0.3% in chloroform).

Analysis: Calculated: %C, 81.44; %H, 8.70. Found: %C, 81.4; %H, 8.9.

EXAMPLE 36

(17R,2'S)2'-oxido-10β-(1-propynyl)-spiro-[Δ$^{4,9(11)}$-estradien-17,5'-1,2-oxathiolane]-3-one (isomer A) and (17R,2'R)-2'-oxido-10β-(1-propynyl)-spiro-[Δ$^{4,9(11)}$-estradien-17,5'-1,2-oxathiolane]-3-one (isomer B)

STEP A:

17S-3,3-ethylenedioxy-10β-propynyl-spiro-[Δ$^{9(11)}$-estren-17,2'-oxiran]-5α-ol At ambient temperature and under an atmosphere of nitrogen, 16.8 ml of a 2.4M solution in tetrahydrofuran of potassium tert.-butylate were added over 10 minutes to 10 g of 3,3-ethylenedioxy-10β-(1-propynyl)-Δ$^{9(11)}$-estren-5α-ol-17-one of Step A of Example 4 in 140 ml of tetrahydrofuran. Then, 6.88 g of trimethyl sulfonium iodide in 138 ml of dimethyl sulfoxide were added with stirring over 1 hour. The mixture was poured into 200 ml of an iced aqueous solution half saturated with ammonium chloride and was extracted with ether. The organic phase was washed with water, then with a saturated aqueous solution of sodium chloride, dried and concentrated to dryness. The residue was chromatographed over silica and was eluted with n-hexaneethyl acetate 7-3 with 1 o/oo of triethylamine to obtain 8.79 g of 17S-3,3-ethylenedioxy-10β-propynyl-spiro-[Δ$^{9(11)}$-estren-17,2'-oxiran]-5α-ol.

STEP B:
3,3-ethylenedioxy-10β-ethynyl-17α-(tert.-butylsulfinylethyl)-Δ$^{9(11)}$-estraene-5α,17β-diol At 5° C. and over a period of 70 minutes, 98.8 ml of a 1.6M solution of butyllithium in hexane were added to 19.6 ml of methyl-butylsulfoxide in 164 ml of tetrahydrofuran and the mixture was stirred for 15 minutes. Over 10 minutes, a solution of 3.13 g of the product of Step A in 16.2 ml of tetrahydrofuran was added followed by stirring for 10 minutes while keeping the temperature at +5° C. and then allowing it to return to ambient. The reaction medium was stirred for 89 hours and then was cooled to 5° C. and 50 ml of a saturated aqueous solution of ammonium chloride were added with care, followed by extraction with ethyl acetate. The extracts were washed with water, then with a saturated aqueous solution of sodium chloride, dried and concentrated to dryness under reduced pressure. The residue was chromatographed over silica and eluted with methylene chloride-acetone 6-4 with 1 oo/oo of triethylamine to obtain 1.19 g of isomer A and 2.3 g of isomer B (impure).

STEP C:
10β-ethynyl-17α-(tert.-butyl)-sulfinylethyl)-Δ$^{4,9(11)}$-estradien-17β-ol-3-one (isomer A)

1.2 g of isomer A of Step B were heated for 90 minutes at 50° C. in 20 ml of ethanol and 20 ml of 5N hydrochloric acid. After cooling, adding ammonia and partially concentrating, extraction was effected with methylene chloride. The organic phase was washed with water, then with a saturated aqueous solution of sodium chloride, dried, and concentrated to dryness. The residue was taken up in 20 ml of methanol, heated to reflux, cooled, separated and dried to obtain 0.92 g of 10β-ethynyl-17α-(tert.-butyl)-sulfinylethyl)-Δ$^{4,9(11)}$-estradien-17β-ol-3-one (isomer A) melting at 178° C.

10β-ethynyl-17α-(tert.-butyl)-sulfinylethyl)-Δ$^{4,9(11)}$-estradien-17β-ol-3-one (isomer B)

2.3 g of isomer B of Step B were heated for 2 hours at 50° C. in 68 ml of ethanol and 17 ml of 5N hydrochloric acid and the mixture was cooled and poured into iced water and extracted with ethyl acetate. The organic phase was washed with water, then with a saturated aqueous solution of sodium chloride, dried and concentrated to dryness. The residue was chromatographed over silica and eluted with methylene chloride-acetone (6-4) to obtain 1.266 g of 10β-ethynyl-17α-(tert.-butylsulfinylethyl)-Δ$^{4,9(11)}$-estradien-17β-ol-3-one which after solidification from ether melted at 165°–166° C.

STEP D: (17R,2'S)
2'-oxido-10β-(1-propynyl)-spiro-[Δ$^{4,9(11)}$-estradien-17,5'-1,2-oxathiolane]-3-one (isomer A)

0.415 g of N-chlorosuccinimide were added to a solution of 1.233 g of isomer B of Step C, 15 ml of tetrahydrofuran and 7 ml of water and after stirring for 35 minutes, the mixture was diluted with water and extracted with methylene chloride. The organic phase was washed with water, then with a saturated aqueous solution of sodium chloride, dried and concentrated to dryness under reduced pressure. The residue was chromatographed over silica and eluted with ethyl acetate-cyclohexane 7-3 to obtain 1.06 g of crude product. The latter was taken up in 6 ml of ethanol, concentrated to initiate crystallization, then cooled, separated and dried to obtain 0.586 g of (17R,2'S) 2'-oxido-10β-(1-propynyl)-spiro-[Δ$^{4,9(11)}$-estradien-17,5'-1,2-oxathiolane]-3-one melting at 210° C. and having a specific rotation of $[\alpha]_D = -5.5° \pm 2°$ (c=0.5 in chloroform).

Analysis: Calculated: %C, 71.84; %H, 7.34; %S, 8.34. Found: %C, 72.1; %H, 7.4; %S, 8.3.

STEP E: (17R,2'R)
2'-oxido-10β-(1-propynyl)-spiro-[Δ$^{4,9(11)}$-estradien-17,5'-1,2-oxothiolane]-3-one (isomer B)

Using the procedure of Step D (1), 1.068 g of the isomer A of Step C (1) in 15 ml of tetrahydrofuran, 7 ml of water and 0.415 g of N-chlorosuccinimide was reacted to obtain 0.48 g of (17R,2'R) 2'-oxido-10β-(1-propynyl)-spiro-[Δ$^{4,9(11)}$-estradien-17,5'-1,2-oxothiolane]-3-one metling at 198° C. and having a specific rotation of $[\alpha]_D = +3.5° \pm 2°$ (c=0.5% in chloroform).

Analysis: Calculated: %C, 71.84; %H, 7.34; %S, 8.34. Found: %C, 71.5; %H, 7.5; %S, 8.2.

EXAMPLE 37
(17S)
3'-propyl-10β-(1-propynyl)-spiro-[Δ$^{4,9(11)}$-estradien-17,5'-oxazolidine]-2',3-dione

STEP A:
3,3-ethylenedioxy-10β-(1-propynyl)-17α-(propylaminomethyl)-Δ$^{9(11)}$-estrene-5α,17β-diol 3 g of (17S) 3,3-ethylenedioxy-10β-(1-propynyl)-spiro-[Δ$^{9(11)}$-estren-17.2'-oxiran]-5α-ol of Step A of Example 36 and 68 mg of p-toluenesulfonic acid were heated for 4 hours at 140° C. in 4.1 ml of toluene and 5.7 ml of propylamine and then was cooled in an ice bath. After extraction with methylene chloride, the organic phase was washed with aqueous solution of sodium bicarbonate, then with water, dried and concentrated to dryness under reduced pressure. The residue was chromatographed over silica and eluted with methylene chloride-methanol-ammonia to obtain 3.33 g of 3,3-ethylenedioxy-10β-(1-propynyl)-17α-(propylaminomethyl)-Δ$^{9(11)}$-estrene-5α,17β-diol.

STEP B:
3,3-ethylenedioxy-10β-(1-propynyl)-17α-[N-propyl-N-(ethoxycarbonyl)-amino]-methyl-Δ$^{9(11)}$-estraene-5α,17β-diol In an atmosphere of nitrogen and over a period of 40 minutes, 11.5 ml were added to 3.3 g of the product of Step A in 35 ml of a solution of triethylamine in chloroform (10-1) and after stirring for 45 minutes, the mixture was diluted with an aqueous solution of sodium bicarbonate, decanted, and the chloroform phase was washed with water and then with an aqueous solution of sodium bicarbonate, decanted, and the chloroform phase was washed with water and then with an aqueous solution of sodium chloride. After drying and concentrating to dryness under reduced pressure, the residue was chromatographed over silica and was eluted with hexane-ethyl acetate (6-4) with 1 o/oo of triethylamine to obtain 3.62 g of 3,3-ethylenedioxy-10β-(1-propynyl)-17α-[N-propyl-N-(ethoxycarbonyl)]-amino-methyl.

STEP C:

3,3-ethylenedioxy-(17S)-3'-propyl-10β-(1-propynyl)-spiro-Δ$^{9(11)}$-estraen-5α-ol-17,5'-oxazolidine-2'-one 3.6 g of the product of Step B were refluxed for 1 hour under an atmosphere of nitrogen in 35 ml of a 0.5M solution of potassium hydroxide in methanol. After adding iced water, the pH was adjusted to 6 with N hydrochloric acid and was extracted with ethyl acetate. The organic phase was washed with water and then with a saturated aqueous solution of sodium chloride. After drying and concentrating to dryness under reduced pressure, 3.25 g of 3,3-ethylenedioxy-(17S)-3'-propyl-10β-(1-propynyl)-spiro-Δ$^{9(11)}$-estraen-5-ol-17,5'-oxazolidine-2'one. were obtained.

STEP D: (17S)

3'-propyl-10β-(1-propynyl)-spiro-[Δ$^{4,9(11)}$-estradien-17,5'-oxazolidine]-2',3-dione Using the procedure of Step B of Example 35, 3.2 g of the product of Step C, 71 ml of ethanol and 18 ml of 5N hydrochloric acid were reacted to obtain 2.56 g of crude product which was triturated in n-pentane and dried to obtain 2.32 g of (17S) 3'propyl-10β-(1-propynyl)-spiro-[Δ$^{4,9(11)}$-estradien-17,5'-oxazolidine]-2',3-dione melting at 150° C. after crystallization from isopropyl ether and having a specific rotation of $[\alpha]_D = -8.5° \pm 0.5°$ (c=1% in chloroform).

Analysis: Calculated: %C 76.63; %H, 8.16; %N, 3.43. Found: %C, 76.4; %H, 8.3; %N, 3.4.

EXAMPLE 38

γ-lactone of 10β-ethynyl-19-nor-Δ$^{1,4,9(11)}$-pregnatrien-17β-ol-3-one-21-carboxylic acid 1 g of the product of Step C of Example 1, 50 ml of benzene, 1.4 g of dichlorodicyanoquinone and 0.6 g of benzoic acid were refluxed for 24 hours and the solution was then cooled, and after adding 10 ml of N sodium hydroxide, was extracted with ethyl acetate. The organic phase was washed with water and then with a saturated aqueous solution of sodium chloride, dried and concentrated to dryness under reduced pressure. The residue was chromatographed over silica and eluted with methylene chloride-acetone 95-5 to obtain 508 mg of γ-lactone of 10β-ethynyl-19-nor-Δ$^{1,4,9(11)}$-pregnatrien-17β-ol-3-one-21-carboxylic acid which after crystallization from ethyl acetate melted at 230° C.

| IR Spectrum (chloroform) |
| --- |
| 3305 cm$^{-1}$: —C≡CH: |
| 1766 cm$^{-1}$ —C=O ⎰ γ-lactone |
| 1669 cm$^{-1}$ ⎱ conjugated ketone. |
| 1634–1610 cm$^{-1}$: —C=C—; |
| 891 cm$^{-1}$ —C=C Δ1,4 |

EXAMPLE 39

γ-lactone of 10β-(2-bromoethynyl)-19-nor-17α-Δ$^{4,9(11)}$-pregnadien-17β-ol-3-one-21-carboxylic acid 178 mg of N-bromosuccinimide and 16 mg of silver nitrate were added to a solution of 280 mg of the product of Example 1 in 6 ml of acetone and after stirring for one hour at ambient temperature, the reaction medium was diluted with water. A 10% aqueous solution of sodium thiosulfate was added and the mixture was extracted with methylene chloride. The extracts were dried and concentrated to dryness, and the residue was solidified in isopropyl ether to obtain 250 mg of γ-lactone of 10β-(2-bromoethynyl)-19-nor-17α-Δ$^{4,9(11)}$-pregnadien-17β-ol-3-one-21-carboxylic acid having a specific rotation of $[\alpha]_D + 23.5°$ (c=1% in chloroform).

Analysis: $C_{23}H_{25}BrO_3$; molecular weight=429.36. Calculated: %C, 64.34; %H, 5.86; %Br, 18.61. Found: %C, 64.3; %H, 5.9; %Br, 18.4.

EXAMPLE 40

Example of Pharmaceutical Composition

Tablets were prepared with 50 mg of the product of Example 4 as active principle and sufficient excipient of talc, starch and magnesium stearate for a final weight of 100 mg.

PHARMACOLOGICAL STUDY

Study of anti-aldosterone activity on the mineralo-corticoid receptor of rat kidney Male Sprague-Dawley EPOS rats weighing 140 to 160 g suprarenalectomized 4 to 6 days earlier were killed and their kidneys were perfused in situ with 50 ml of a Tris buffer, 10 m M-saccharose 0.25M HCl pH 7.4. Their kidneys were then removed, decapsulated and homogenized at 0° C. by means of a Potter ptfe-glass (1 g of tissue for 3 ml of buffer). The homogenate was centrifuged for 10 minutes at 800 g at 0° C. To eliminate the fixation of the tritiated aldosterone on the glucocorticoid receptor, 21-methyl-Δ$^{1,4,6}$-pregnatriene-11β,17β-diol-20-yn-3-one which fixed uniquely on the glucocorticoid receptor was added to the supernatant at the final concentration of $10^{-6}$. This supernatant was ultra-centrifuged at 105,000 g for 60 minutes at 0° C. Equal quantities of the supernatant so obtained were incubated at 0° C. with a constant concentration (T) of tritiated aldosterone in the presence of increasing concentrations (0–2500 $10^{-9}$M) of cold aldosterone or of the cold product under study. After an incubation time (t), the concentration of bonded tritiated aldosterone (B) was measured by the technique of adsorption on dextran-carbon.

Calculation of the relative affinity of bond

The calculation of the relative affinity of bond (RAB) was carried as follows: The two following curves were traced: the percentage of tritiated hormone bonded B/T as a function of the logarithm of the concentration of the cold reference hormone, and B/T as a function of the logarithm of the concentration of the cold product under test. The straight line was determined of the equation $$I^{50} = \left( \frac{B}{T} \max + \frac{B}{T} \min \right) / 2$$

(B/T) max=percentage of tritiated hormone bonded for an incubation of this tritiated hormone at the concentration (T). (B/T) min.=percentage of tritiated hormone bonded for an incubation of this tritiated hormone at the concentration (T) in the presence of a great excess of cold hormone (2500.10$^{-9}$M). The intersections of the straight line $I^{50}$ and of the curves enabled the concentrations of the cold reference hormone (CH) and the cold product under test (CX) to be evaluated which inhibited by 50% the bonding of the tritiated hormone on the receptor. The relative affinity of bonding (RAB) of the product under test was determined by the equation $$RAB = 100 \frac{(CH)}{(CX)}$$

The following results were obtained.

| Product of example | Time of incubation at 0° C. | |
| --- | --- | --- |
| | 4 Hours | 24 Hours |
| 1 | 510 | 165 |
| 4 | 70 | 63 |
| 6 | 240 | 19 |
| 8 | 273 | 64 |
| 9 | 46 | 96 |
| 15 | 151 | 5 |
| Product P | 164 | 13 |

Product P is 10β-(ethynyl)-Δ$^{4,9(11)}$-estradiene-17β-ol-3-one described in Bull. Soc. Chim. Fr. (1970), No. 7, page 2556.

Various modifications of the products and methods of the invention may be made without departing from the spirit or scope thereof and it is to be understood that the invention is intended to be limited only as defined in the appended claims.

What we claim is:

1. A compound 10-substituted steroids of the formula I

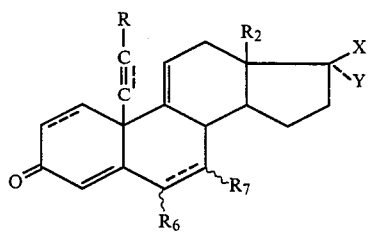

wherein R is selected from the group consisting of hydrogen, alkyl and substituted alkyl of 1 to 8 carbon atoms, alkenyl, substituted alkenyl, alkynyl and substituted alkynyl of 2 to 8 carbon atoms, aryl and substituted aryl, aralkyl and substituted aralkyl, protected hydroxy, optionally esterified carboxy, —NH$_2$ protected amino, mono and di-alkyl amino of 1 to 4 alkyl carbon atoms, halogen and trialkylsilyl, $R_2$ is methyl or ethyl, $R_6$ and $R_7$ together with the carbon atoms to which they are attached form cyclopropyl or $R_6$ is hydrogen and $R_7$ is $R_1$, $R_1$ is selected from the group consisting of hydrogen, alkyl and substituted alkyl of 1 to 6 carbon atoms, acetylthio and alkenyl, substituted alkenyl, alkynyl and substituted alkynyl of 2 to 6 carbon atoms, X is optionally acylated or etherified hydroxyl and Y is selected from the group consisting of hydrogen, $R_4$, —CH$_2$—CH$_2$COOM and —CH$_2$—CH$_2$—CH$_2$OH, M is hydrogen, alkali metal or —NH$_4$ or X and Y together form a member of the group consisting of

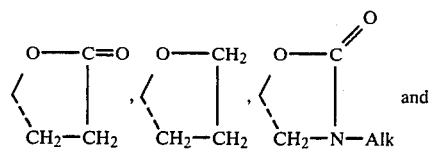

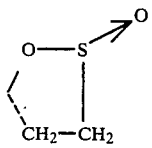

or X is —OH and Y is

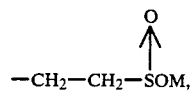

$R_4$ is selected from the group consisting of alkyl of 1 to 6 carbon atoms and alkenyl and alkynyl of 2 to 6 carbon atoms, Alk is alkyl of 1 to 8 carbon atoms, the dotted lines in the 1(2) and 6(7) indicate the optional presence of a second carbon-carbon bond, the dotted line in the 10-substituent indicates the optional presence of a third carbon-carbon bond, and the wavy lines at $R_6$ and $R_7$ indicate the possibility of either α or β orientation; with the proviso that when $R_6$ and $R_7$ form cyclopropyl, there is no double bond at the 6(7) position, and with the additional proviso that R is not hydrogen when $R_6$ and $R_7$ are hydrogen, $R_2$ is methyl, X is hydroxy or acetoxy, Y is hydrogen, the dotted lines at 1(2) and 6(7) do not represent a second bond, and the dotted line in the 10-substituent is a third carbon-carbon bond.

2. A compound of claim 1 answering to the formula $I_1$

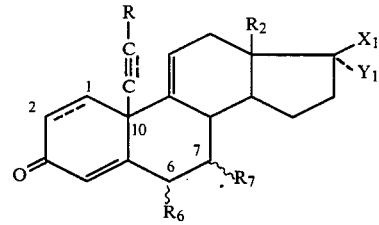

wherein $X_1$ is —OH and $Y_1$ is —CH$_2$—CH$_2$—COOM or —CH$_2$—CH$_2$—CH$_{2OH,M}$ has the above definition or $X_1$ and $Y_1$ together form

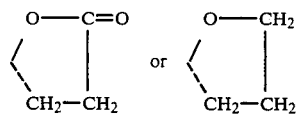

or $X_1$ is optionally acylated or etherified hydroxyl and $Y_1$ is hydrogen or $R_4$ and $R_4$ has the above definition and the dotted lines in the 1(2) and 6(7) and in the 10-substituent have the above definition and the wavy lines have the above definition with the proviso that R is not hydrogen when $R_6$ and $R_7$ are hydrogen, $R_2$ is methyl, $X_1$ is —OH or acetoxy, $Y_1$ is hydrogen and the 1(2) and 6(7) positions are saturated and the dotted line in the 10-substituent is a third carbon-carbon bond.

3. A compound of claim 2 wherein $R_6$ is hydrogen and $R_7$ is $R_1$.

4. A compound of claim 1 or 3 wherein R and $R_1$ are individually selected from the group consisting of —OH, optionally esterified carboxy, —$NH_2$, protected amino, halogen and mono- and di-alkylamino with 1 to 4 alkyl carbon atoms.

5. A compound of claim 1 or 2 wherein the dotted line in the 10-substituent is a third carbon-carbon bond and $R_2$ is selected from the group consisting of hydrogen, alkyl of 1 to 3 carbon atoms, methylhydroxy and phenyl.

6. A compound of claim 1 or 2 wherein $R_1$ is selected from the group consisting of hydrogen, alkyl of 1 to 4 carbon atoms and acetylthio and X is —OH and Y is hydrogen or —$CH_2$—$CH_2$—COOM' and M' is hydrogen or alkali metal or X and Y together form

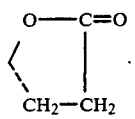

7. A compound of claim 1 selected from the group consisting of γ-lactone of 10β-ethynyl-19-nor-17α-$\Delta^{4,9(11)}$-pregnadiene-17β-ol-3-one-21-carboxylic acid and the γ-lactone of 10β-(1-propynyl)-19-nor-17α-$\Delta^{4,9(11)}$-pregnadiene-17β-ol-3-one-21-carboxylic acid.

8. A composition for treating arterial hypertension and cardiac insufficiencies comprising an effective amount of at least one compound of claim 2 and an inert pharmaceutical carrier.

9. A composition of claim 8 wherein $R_6$ is hydrogen and $R_7$ is $R_1$.

10. A composition of claim 8 wherein R and $R_1$ are individually selected from the group consisting of —OH, optionally esterified carboxy, —$NH_2$, protected amino, halogen and mono- and di-alkylamino with 1 to 4 carbon atoms.

11. A composition of claim 8 wherein the dotted line in the 10-substituent is a third carbon-carbon bond and $R_2$ is selected from the group consisting of hydrogen, alkyl of 1 to 3 carbon atoms, methylhydroxy and phenyl.

12. A composition of claim 8 wherein $R_1$ is selected from the group consisting of hydrogen, alkyl of 1 to 4 carbon atoms and acetylthio and X is —OH and Y is hydrogen or —$CH_2$—$CH_2$—COOM' and M' is hydrogen or alkali metal or X and Y together form

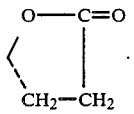

13. A composition of claim 8 wherein the active compound is selected from the group consisting of γ-lactone of 10β-ethynyl-19-nor-17α-$\Delta^{4,9(11)}$-pregnadiene-17β-ol-3-one-21-carboxylic acid and the γ-lactone of 10β-(1-propynyl)-19-nor-17α-$\Delta^{4,9(11)}$-pregnadiene-17β-ol-3-one-21-carboxylic acid.

14. A method of treating arterial hypertension and cardiac insufficiencies in warm-blooded animals comprising administering to warm-blooded animals an amount of at least one compound of claim 2 sufficient to treat arterial hypertension and cardiac insufficiencies.

15. A method of claim 14 wherein $R_6$ is hydrogen and $R_7$ is $R_1$.

16. A method of claim 14 wherein R and $R_1$ are individually selected from the group consisting of —OH, optionally esterified carboxy, —$NH_2$, protected amino, halogen and mono- and di-alkylamino with 1 to 4 alkyl carbon atoms.

17. A method of claim 14 wherein the dotted line in the 10-substituent is a third carbon-carbon bond and $R_2$ is selected from the group consisting of hydrogen, alkyl of 1 to 3 carbon atoms, methylhydroxy and phenyl.

18. A method of claim 14 wherein $R_1$ is selected from the group consisting of hydrogen, alkyl of 1 to 4 carbon atoms and acetylthio and X is —OH and Y is hydrogen or —$CH_2$—$CH_2$—COOM' and M' is hydrogen or alkali metal or X and Y together form

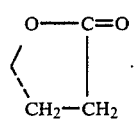

19. A method of claim 14 selected from the group consisting of γ-lactone of 10β-ethynyl-19-nor-17α-$\Delta^{4,9(11)}$-pregnadiene-17β-ol-3-one-21-carboxylic acid and the γ-lactone of 10β-(1-propynyl)-19-nor-17α-$\Delta^{4,9(11)}$-pregnadiene-17β-ol-3-one-21-carboxylic acid.

20. A composition for inducing aldosterone atagonistic activity comprising an effective amount of at least one compound of formula (I') and an inert pharmaceutical carrier,

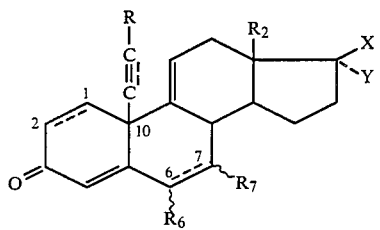

wherein R is selected from the group consisting of hydrogen, alkyl and substituted alkyl of 1 to 8 carbon atoms, alkenyl, substituted alkenyl, alkynyl and substituted alkynyl of 2 to 8 carbon atoms, aryl and substituted aryl, aralkyl and substituted aralkyl, protected hydroxy, optionally esterified carboxy, —$NH_2$, protected amino, mono and di-alkyl amino of 1 to 4 alkyl carbon atoms, halogen and trialkylsilyl, $R_2$ is methyl or ethyl, $R_6$ and $R_7$ together with the carbon atoms to which they are attached form cyclopropyl or $R_6$ is hydrogen and $R_7$ is $R_1$, $R_1$ is selected from the group consisting of hydrogen, alkyl and substituted alkyl of 1 to 6 carbon atoms, acetylthio and alkenyl, substituted alkenyl, alkynyl and substituted alkynyl of 2 to 6 carbon atoms, X is optionally acylated or etherified hydroxyl and Y is selected from the group consisting of hydrogen, $R_4$, —$CH_2$—$CH_2COOM$ and —$CH_2$—$CH_2$—$CH_2OH$, M is hydrogen, alkali metal or —$NH_4$ or X and Y together form a member of the group consisting of

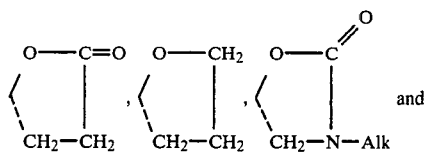 and

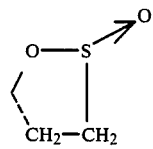

or X is —OH and Y is

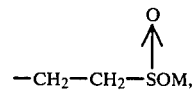

$R_4$ is selected from the group consisting of alkyl and 1 to 6 carbon atoms and alkenyl and alkynyl of 2 to 6 carbon atoms, Alk is alkyl of 1 to 8 carbon atoms, the dotted lines in the 1(2) and 6(7) indicate the optional presence of a second carbon-carbon bond, the dotted line in the 10-substituent indicates the optional presence of a third carbon-carbon bond and the wavy lines at $R_6$ and $R_7$ indicate the possibility of either α or β orientation; with the proviso that when $R_6$ and $R_7$ form cyclopropyl, there is no double bond at the 6(7) position.

21. A method of inducing aldosterone antagonistic activity in warm-blooded animals comprising administering to warm-blooded animals an aldosterone antogonistically effective amount of at least one compound of formula (I') as defined in claim 20.

* * * * *

UNITED STATES PATENT AND TRADEMARK OFFICE
CERTIFICATE OF CORRECTION

PATENT NO. : 4,701,449   Page 1 of 3

DATED : Oct. 20, 1987

INVENTOR(S) : VESPERTO TORELLI, LUCIEN NEDELEC, MARTINE MOGUILEWSKI and ANNE-MARIE MOURA It is certified that error appears in the above-identified patent and that said Letters Patent is hereby corrected as shown below:

| Col. | Line | |
|---|---|---|
| [57] | 15 Abstract | "$CH_2-CH_2-CH_2OH$" should be -- $-CH_2-CH_2-CH_2-OH$ -- |
| 1 | 58&59 | "  "  "  "  "  "  "  "  "  "  "  "  "  "  "  "  " |
| 2 | 45&46 | "  "  "  "  "  "  "  "  "  "  "  "  "  "  "  "  " |
| 4 | 10 | Delete one of "17α" |
| 4 | 11 | "17β61" should be --17β-ol-- |
| 8 | Formula I4C | 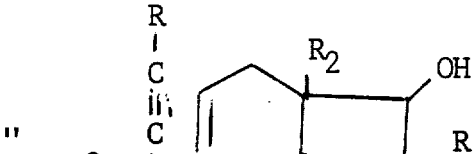 " should be 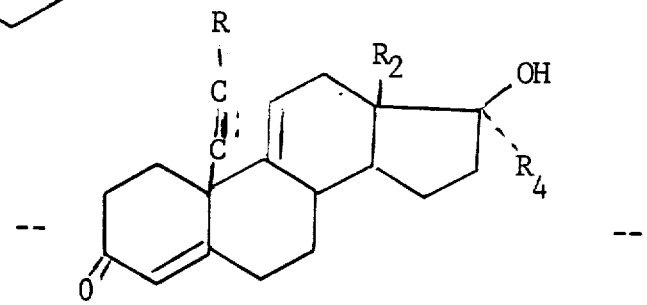 |

UNITED STATES PATENT AND TRADEMARK OFFICE
CERTIFICATE OF CORRECTION

PATENT NO. : 4,701,449

DATED : Oct. 20, 1987

INVENTOR(S) : VESPERTO TORELLI, LUCIEN NEDELEC, MARTINE MOGUILEWSKI and ANNE-MARIE MOURA It is certified that error appears in the above-identified patent and that said Letters Patent is hereby corrected as shown below:

| Col. | Line | Formula | | |
|---|---|---|---|---|
| 10 | | $I_{6D}$ | | "  " should be -- 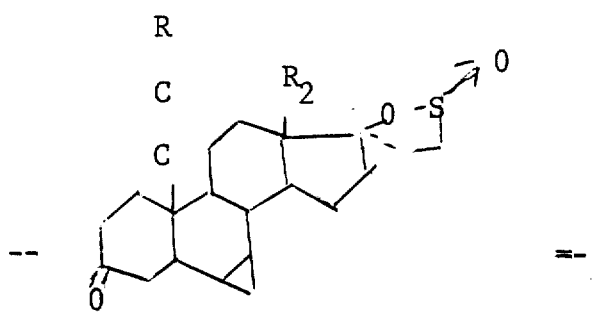 =-- |
| 14 | 7 | 21 | 25 | "R'-C≡C-Li" should be --R'-C≡C-Li-- |
| 16 | 6&7 | 25 | 15 | "-$CH_2$-$CH_2$-CH-2" should be --$CH_2$-$CH_2$-$CH_2$- -- |
| 17 | 36 | 27 | 13 | "142° C" should be --142°C-- |
| 19 | 33&34 | 31 | 10 | "204° C " should be --204°C-- |
| 19 | 58&59 | 32 | 1 | "60-80° C" should be --60°-80°C-- |
| 20 | 30 | 33 | 5 | Delete one "B" |

UNITED STATES PATENT AND TRADEMARK OFFICE
CERTIFICATE OF CORRECTION

PATENT NO. : 4,701,449        Page 3 of 3

DATED     : Oct. 20, 1987

INVENTOR(S) : VESPERTO TORELLI, LUCIEN NEDELEC, MARTINE MOGUILEWSKI and ANNE-MARIE MOURA It is certified that error appears in the above-identified patent and that said Letters Patent is hereby corrected as shown below:

| Col. | Line |  |
|---|---|---|
| 29 | 64 | "undeer" should be --under-- |
| 30 | 50 | "etjyl" should be --ethyl-- |
| 31 | 34 | "cryness" should be --dryness-- |
| 32 | 34 | "hyclohexane" should be --cyclohexane-- |
| 41 | Claim 1 | "-$CH_2$-$CH_2$-$CH_2$" should be -- -$CH_2$-$CH_2$-$CH_2$- -- |
| 44 | Claim 78A 20 | 19 " " " " " " " " " " " " " " " " " "" " " " |

Signed and Sealed this

Twenty-sixth Day of July, 1988

Attest:

DONALD J. QUIGG

Attesting Officer         Commissioner of Patents and Trademarks